United States Patent [19]
Radziejewski et al.

[11] Patent Number: 6,022,694
[45] Date of Patent: Feb. 8, 2000

[54] ASSAY FOR LIGANDS TO TYROSINE KINASE RECEPTORS

[75] Inventors: Czeslaw Radziejewski, Somers, N.Y.; Ajay Shrivastava, Fairfield, Conn.; George D. Yancopoulos, Yorktown Heights, N.Y.

[73] Assignee: Regeneron Pharmaceuticals, Inc., Tarrytown, N.Y.

[21] Appl. No.: 08/998,972

[22] Filed: Dec. 29, 1997

Related U.S. Application Data

[60] Provisional application No. 60/042,610, Apr. 4, 1997.

[51] Int. Cl.$^7$ ........................................................ C12Q 1/00
[52] U.S. Cl. .......................... 435/7.1; 435/194; 435/7.15; 530/350
[58] Field of Search .................................... 435/7.1, 69.1, 435/194, 7.9, 7.92, 7.94, 7.15; 530/350

*Primary Examiner*—Sally P. Teng
*Attorney, Agent, or Firm*—Robert J. Cobert; Gail Kempler

[57] ABSTRACT

The present invention provides for a screen for a polypeptide ligand that can bind to the Tyro-10 (DDR-2) or NEP (DDR-1) receptor and that can promote a differential function and/or influence the phenotype, such as growth and/or proliferation, of cells that bear the receptor. The present invention also provides a method of screening for a molecule capable of competing with collagen for binding to the extracellular domain of a Tyro-10 (DDR-2) or NEP (DDR-1) receptor comprising contacting a sample suspected of containing the molecule with the extracellular domain of a Tyro-10 (DDR-2) or NEP (DDR-1) receptor in the presence of collagen under conditions in which the collagen is capable of binding to the extracellular domain and detecting binding of the molecule to the Tyro-10 (DDR-2) or NEP (DDR-1) receptor extracellular domain. The invention further contemplates the utilization of collagen to support the growth, survival, or differentiation of Tyro-10 (DDR-2) or NEP (DDR-1) expressing cells.

3 Claims, 12 Drawing Sheets

Fig. 6A

|  | Total Protein (mg) | Total Collagen (mg) |
|---|---|---|
| A204 cond. media (1000ml) | 337.1 | 13.4 |
| ↓ | | |
| Cation Exchange (HiTrapS Retentate) | 50.5 | 3.9 |
| ↓ | | |
| 20mM $CaCl_2$ Precip. | ND | 4.2 |
| ↓ | | |
| Pepsin Digestion | ND | ND |
| ↓ | | |
| 4.5M NaCl Precip. | ND | 0.35 |
| ↓ | | |
| Sizing Column (Peak A) (S6 gel filtr. in urea) | 0.33 | 0.3 |

Fig. 6B

| Amino Acid Residue | A204 Protein (mole%) | Bovine Coll. I (mole%) | Human $[\alpha_1(XI)]_2\alpha_2(V)$ (mole%) |
|---|---|---|---|
| ASX | 5.4 | 4.7 | 4.7 |
| GLX | 10.2 | 7.0 | 9.4 |
| SER | 2.7 | 3.6 | 2.5 |
| HIS | 1.1 | 0.9 | 0.6 |
| GLY | 29.9 | 26.5 | 34.3 |
| THR | 1.9 | 1.8 | 2.0 |
| ALA | 6.2 | 11.2 | 5.1 |
| ARG | 4.3 | 5.4 | 4.4 |
| TYR | 0.6 | 0.4 | 0.2 |
| VAL | 2.8 | 2.1 | 2.6 |
| MET | 1.1 | 0.8 | 1.0 |
| PHE | 1.5 | 1.3 | 1.0 |
| ILE | 1.9 | 1.3 | 1.3 |
| LEU | 4.1 | 2.5 | 3.4 |
| LYS | 2.4 | 2.3 | } 4.9 |
| HYL | ND | ND | |
| HYP | 11.2 | 15.6 | } 22.2 |
| PRO | 12.6 | 12.6 | |

Fig. 11A
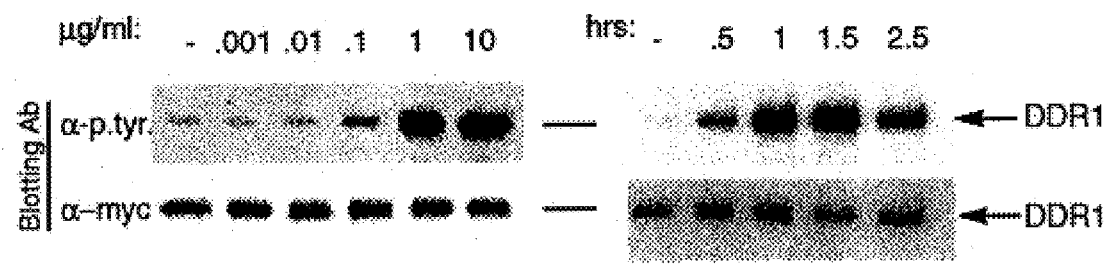
Fig. 11B
Fig. 11C
Fig. 11D

ASSAY FOR LIGANDS TO TYROSINE KINASE RECEPTORS

This application claims priority of U.S. Provisional Application Ser. No. 60/042,610 filed Apr. 4, 1997. Throughout this application, various references are cited, the disclosures of which are hereby incorporated by reference in their entireties.

The present invention provides an assay or screen for identifying ligands that bind the Tyro-10 (also designated DDR-2) or NEP (also designated DDR-1) receptor tyrosine kinases. The ligand may be an agonist or an antagonist. It is based on applicants' discovery that collagen is a ligand for the Tyro-10 (DDR-2) and NEP (DDR-1) receptors.

BACKGROUND OF THE INVENTION

Mammalian cells must integrate, and respond to, a myriad of signals from their microenvironment. Many of these signals are sensed by receptors expressed on the surface of the responding cell. Two critical classes of cell surface receptors include those known as "receptor tyrosine kinases" and those classified as "integrins". Receptor tyrosine kinases recognize and respond to peptide growth factors such as insulin, platelet-derived growth factor and nerve growth factor (Ullrich and Schlessinger, 1990), while the integrins most often mediate binding and attachment to components of the extracellular matrix such as collagen, fibronectin, and vitronectin (Clark and Brugge, 1995). There is increasing evidence that receptor tyrosine kinases and integrins act in coordinated fashion to modulate cellular responses involving adhesion, spreading, locomotion, proliferation, survival and differentiation state (Clark and Brugge, 1995).

Receptor tyrosine kinases are thus named because of the tyrosine kinase domain found in the cytoplasmic portion of these receptors (Ullrich and Schlessinger, 1990). Ligand binding to the receptor ectodomain results in activation of the tyrosine kinase domain, which in turn leads to recruitment and activation of a variety of downstream signaling molecules. A number of receptor-like tyrosine kinases have been molecularly cloned based on the homologies shared by the tyrosine kinase domains of all receptors in this class (e.g., Lai and Lemke, 1991). Although presumed to have ligands, these receptor-like proteins are termed "orphans" until their ligands are indeed identified. A variety of approaches have led to the identification of ligands for previously orphan receptors. For example, the ephrins have been identified as the ligands for the EPH family of receptors (Bartley et al., 1994; Beckmann et al., 1994; Davis et al., 1994; Cheng and Flanagan, 1994), Protein S and Gas6 have been identified as ligands for the Tyro3/Sky/rse/brt/tf and Axl/Ark/UFO receptors (Stitt et al., 1995; Varnum et al., 1995), agrin has been identified as the ligand for MuSK (Glass et al., 1996), glial-derived neurotrophic factor has been identified as the ligand for the Ret receptor (Jing et al., 1996; Treanor et al., 1996), and the angiopoietins have been identified as the ligands for the Tie receptors (Davis et al., 1996; Maisonpierre et al., 1997).

Among the few remaining orphan receptor-like tyrosine kinases are two close relatives which are distinguished by a strucutral domain in their extracellular portions that has not been found in other receptor tyrosine kinases, but was instead first noted in the discoidin I protein of the slime mold *Dictyostelium discoideum* (Poole et al., 1981) and thus termed the discoidin I domain. Discoidin I domains have more recently been noted to be homologous to the constant regions of blood coagulation Factors V and VIII (Wood et al., 1984; Jenny et al., 1987) and to a neural recognition molecule termed A5 identified in *Xenopus laevis* (Takagi et al., 1987). The two closely related receptor-like tyrosine kinases which contain discoidin I domains have been cloned by several groups and given several different names. We will refer to these receptor-like tyrosine kinases as Discoidin Domain Receptor 1 (DDR1) for the receptor previously termed DDR (Johnson et al., 1993), NEP (Zerlin et al., 1993), Ptk-3 (Sanchez et al., 1994), Cak (Perez et al., 1994), trkE (DiMarco et al., 1993) and MCK-10 (Alves et al., 1995), and Discoidin Domain Receptor 2 (DDR2) for the receptor previously termed Tyro10 (Lai and Lemke, 1991; Lai and Lemke, 1994), TKT (Karn et al., 1993) and CCK-2 (Alves et al., 1995). Previous studies have found that DDR1 and DDR2 are quite widely but differentially expressed during development and in the adult.

Regions of homology in the Trks as well as other RTKs, in combination with the use of PCR technology, has rapidly enabled the cloning of an abundant number of novel protein tyrosine kinases, wherein the cognate ligand has yet to be discovered (hence, such receptors are termed "orphan" receptors). For example, Lai and Lemke (Neuron 6: 691–704 (1991)) identified thirteen novel kinases, designated Tyro-1 through Tyro-13, with several bearing similarity to other known RTKs. Structural comparison indicates that the tyrosine kinase domain of Tyro-10 (DDR-2) is most closely related to the equivalent domains of the Trks. (Lai & Lemke, 1994, Oncogene 9: 877–883). Similarly, Zerlin et al. (Oncogene 8: 2731–2739 (1993)) report the molecular cloning of a cDNA encoding a novel receptor protein tyrosine kinase designated NEP (DDR-1), that is highly expressed in proliferating neuroepithelia. The authors suggested that one function of NEP (DDR-1) kinase is to signal proliferation of neuroepithelial cells in response to an as yet unknown ligand.

Despite the lack of known cognate ligands, knowledge of the tissues in which such orphan receptors are expressed provides insight into the regulation of the growth, proliferation and regeneration of cells in the tissues. Because RTKs appear to mediate a number of important functions associated with development and maintenance, identification of their cognate ligands will inevitably play a crucial role in characterizing these functions.

Ligand-receptor assays are generally useful for the in vitro determination of the presence and concentration of ligands in body fluids, food products, animal fluids, and environmental samples. For example, using such assays to determine the presence and concentration of specific hormones, proteins, therapeutic drugs, and toxic drugs in human blood or urine has significantly improved medical diagnosis.

Ligand-receptor assays rely on the binding of ligands to receptors to determine the presence and/or concentration of ligands in a sample. Ligand-receptor assays can be described as either competitive or non-competitive. Non-competitive assays generally utilize receptors in substantial excess over the concentration of ligand to be determined in the assay. Sandwich assays, in which the ligand is detected by binding to two receptors, one receptor labeled to permit detection and a second receptor frequently bound to a solid phase to facilitate separation from unbound reagents, such as unbound labeled first receptor, are examples of non-competitive assays.

Competitive assays generally utilize ligand from the sample, a ligand analogue labeled to permit detection, and the competition of these species for a limited number of binding sites provided by the ligand receptor. Those skilled in the art will appreciate that many variations of this basic competitive situation have been previously described. Examples of ligands which are commonly measured by competitive ligand-receptor assays include haptens, hormones and proteins. Antibodies or receptorbodies that can bind these classes of ligands are frequently used in these assays as ligand receptors.

Competitive ligand-receptor assays can be further described as being either homogeneous or heterogeneous. In homogeneous assays, all of the reactants participating in the competition are mixed together and the quantity of ligand is determined by its effect on the extent of binding between ligand receptor and labeled ligand analogue. The signal observed is modulated by the extent of this binding and can be related to the amount of ligand in the sample. U.S. Pat. No. 3,817,837 describes such a homogeneous, competitive immunoassay in which the labeled ligand analogue is a ligand-enzyme conjugate and the ligand receptor is an antibody capable of binding to either the ligand or the ligand analogue. The binding of the antibody to the ligand-enzyme conjugate decreases the activity of the enzyme relative to the activity observed when the enzyme is in the unbound state. Due to competition between unbound ligand and ligand-enzyme conjugate for antibody binding sites, as the ligand concentration increases the amount of unbound ligand-enzyme conjugate increases and thereby increases the observed signal. The product of the enzyme reaction may then be measured using a spectrophotometer.

In general, homogeneous assay systems require both an instrument to read the result and calibration of the observed signal by separate tests with samples containing known concentrations of ligand. The development of homogeneous assays has dominated competitive assay research and has resulted in several commercially available systems.

Heterogeneous, competitive ligand-receptor assays require a separation of bound labeled ligand or receptor from the free labeled ligand or receptor and a measurement of either the bound or the free fraction. Methods for performing such assays are described in U.S. Pat. Nos. 3,654,090, 4,298,685, and 4,506,009. U.S. Pat. Nos. 4,125,372, 4,200, 690, 4,246,339, 4,366,241, 4,446,232, 4,477,576, 4,496,654, 4,632,901, 4,727,019, and 4,740,468 describe devices and methods for ligand-receptor assays that develop colored responses for visual interpretation of the results.

In the case of a competitive immunoassay, a labelled antigen reagent is bound to a limited and known quantity of antibody reagent. After that reaction reaches equilibrium, the antigen to be detected is added to the mixture and competes with the labelled antigen for the limited number of antibody binding sites. The amount of labelled antigen reagent displaced, if any, in this second reaction indicates the quantity of the antigen to be detected present in the fluid sample.

Because competitive assays generally result in non-linear response functions, several calibration points are required for such assays in order to determine the response over the assay range. In order to simplify the calibration process, two extreme approaches have evolved. One approach is not to reduce the number of calibrators or replicates needed to determine the response but to reduce the frequency of such calibration. Such assays rely upon instruments to perform the assay and to control variables that affect the assay response so that calibration is infrequent or is performed by the manufacturer and does not need to be performed by the user of the assay. The second approach is to not use an instrument and to provide a simplified means of calibration so that no additional tests are needed to calibrate the assay response.

The method of U.S. Pat. No. 4,540,659 provides an assay for the quantitation of ligand in samples where predetermined ratios of responses at a calibration surface and a measurement surface are related to the concentration of the ligand.

Another approach, a non-competitive immunochromatographic assay, is described in U.S. Pat. Nos. 4,168,146 and 4,435,504. This assay provides a method for quantitatively determining the presence of a single analyte in a sample in a visually interpreted immunoassay. U.S. Pat. No. 5,089,391 describes a method for performing competitive ligand-receptor assays so as to be able to semiquantitatively or quantitatively determine the concentration of the ligand.

SUMMARY OF THE INVENTION

The present invention provides for a screen for a polypeptide ligand that can bind to the Tyro-10 (DDR-2) or NEP (DDR-1) receptor and that can promote a differential function and/or influence the phenotype, such as growth and/or proliferation, of cells that bear the receptor. The invention is based on applicants' discovery that collagen is a cognate ligand for the Tyro-10 (DDR-2) and NEP (DDR-1) receptors. The invention further provides for use of the Tyro-10 (DDR-2) and NEP (DDR-1) receptors and variants thereof, to alter the activity of collagen in a biological system. Such variants include, but are not limited to soluble Tyro-10 (DDR-2) and NEP (DDR-1) receptors and Tyro-10 (DDR-2) and NEP (DDR-1) receptorbodies and chimeras. The invention further contemplates the utilization of collagen to support the growth, survival, or differentiation of Tyro-10 (DDR-2) or NEP (DDR-1) expressing cells.

Applicants' discovery that collagen is a Tyro-10 (DDR-2) and NEP (DDR-1) ligand also enables the skilled artisan to utilize the ligand and receptors for diagnostic utilities. In particular embodiments of the invention, methods of detecting aberrancies in collagen function or expression may be used in the diagnosis of diseases or disorders.

In other embodiments, manipulation of the collagen/Tyro-10 (DDR-2) or collagen/NEP (DDR-1) interaction may be used in the treatment of disorders. For example, fibrosis of the lung and cirrhosis of the liver are each associated with overproduction of collagen. Thus collagen may be involved in regulating these processes. Manipulation of the collagen/Tyro-10 (DDR-2) or collagen/NEP (DDR-1) interaction may be effective in treating these disorders. The present invention may also be useful in treating, for example, Lupus erythematosis, and other chronic disease conditions. Applicants also provide herein an assay useful for screening for collagen antagonists, so that the interaction of collagen with Tyro-10 (DDR-2) or NEP (DDR-1) can be modulated or blocked completely. Since these receptors can distinguish between different collagen types, the present invention provides a screen for identifying a molecule that is capable of modulating or inhibiting the interaction of one collagen type with the receptor but that will not modulate or inhibit the interaction of another collagen type with the receptor.

BRIEF DESCRIPTION OF THE DRAWINGS

FIG. 2A—Tyro-10 (DDR-2) receptorbody was used to stain A204 conditioned media (Lane 1) and commercial collagen type V (Lane 2). FIG. 2B—NEP (DDR-1) receptorbody was used to stain A204 conditioned media (Lane 2) and commercial collagen type V (Lane 1).

FIG. 4A—Mock (−) and 50× Conditioned Medium from A204 cells (+); FIG. 4B—(left to right) Mock (−), Collagen type I from kangaroo tail (K I), Collagen type II from bovine achilles tendon (B II), Collagen type I from calf skin (C I), Collagen type IV from mouse sarcoma (M IV), Collagen type IV from human placenta (H IV), Collagen type I from rat tail (R I), Collagen type I from human placenta (H I), Collagen type V from human placenta (H V), Collagen type III human placenta (H III). Collagen was purchased from Sigma®.

FIG. 5A—Binding of indicated Rbodies to various cell lines identifies cell lines exhibiting cell-associated DDR ligands. Among over 200 lines screened, A204, U373 and Saos2 exhibited elevated binding to both DDR1 and DDR2 Rbodies (albeit to different relative levels) as compared to control Rbodies, while HELA exhibited elevated binding only to DDR1; MG3T3 serves as a control cell line exhibiting elevated binding to one of the control Rbodies, Ehk1-Fc.

FIG. 5B—Binding of radiolabelled DDR2-Fc to cell surfaces can be specifically competed by both DDR1 and DDR2 Rbodies (and not a control Rbody), demonstrating the specificity of binding and that both DDR receptors are binding to the same putative cell-associated ligand.

FIG. 5C—Slot-Blot assay of conditioned media from over 200 cell lines demonstrates specific binding of DDR Rbodies (as compared to control Rbody) only for one cell line (A204, which exhibited highest levels of cell-associated DDR binding), providing source of released ligand.

FIG. 5D—Released ligand in the conditioned media of the A204 cell line specifically induces phosphorylation of full-length DDR1 expressed on COS cells, as compared to control conditioned media (both concentrated 50-fold).

FIG. 6A—Scheme used to purify DDR binding activity from A204 conditioned media; quantitation of total protein and collagen levels during the purification are provided, indicating that purification results in successive enrichment for collagen until it essentially comprises all of protein sample.

FIG. 6B—Amino acid composition of protein purified from A204 conditioned media, as compared to that previously noted for purified Bovine collagen I or theoretically deduced for the collagen previously shown (Kleman, J. -P., et al., 1992, Eur. J. Biochem. 210: 329–335) to be produced by A204 cells (comprised of 2 α1 chains from type XI and 1 α2 chain from type V); note that hydroxylysine levels were not measured, and that the theoretical amino acid composition provided does not distinguish between any hydroxylated residues.

FIGS. 7A & 7B—Silver-stained gel analysis (4–20% SDS PAGE in FIG. 7A, 18% SDS PAGE in FIG. 7B) coupled with DDR slot-blot analysis, of fractions from various steps in the purification scheme outlined in FIG. 6A, as indicated. In FIG. 7B, note that the samples reflect material before and after Superose 6 (S6) size exclusion chromatography, with peaks as indicated in FIG. 7C; most of the DDR binding is evident in peak A.

FIG. 7C—Superose 6 size exclusion chromatography of material from A204 purification procedure (dashed line) as compared to purified, active collagen V (solid line) derived as described in FIG. 9.

FIG. 7D—DDR1 phosphorylation is induced by final purified material (peak A material, see FIG. 7C) obtained from A204 cells (lane 2), abolished when this material is treated with collagenase (lane 3) and comparable to that seen with the purified collagen V (lane 4) derived as described in FIG. 9.

FIG. 11A—Dose-dependence of collagen-induced DDR1 phosphorylation; human type I collagen added to media of DDR1-expressing cells as described in the Examples.

FIG. 11B—Time-dependence of collagen-induced DDR1 phosphorylation; collagen added as in FIG. 11A.

FIG. 11C—Immobilized human type I collagen also induces DDR1 phosphorylation on cells plated on collagen, albeit with slower onset than following added collagen.

FIG. 11D—Control for FIG. 11C, in which cells are plated on dishes that were not previously coated with collagen.

DETAILED DESCRIPTION OF THE INVENTION

Figure 1:
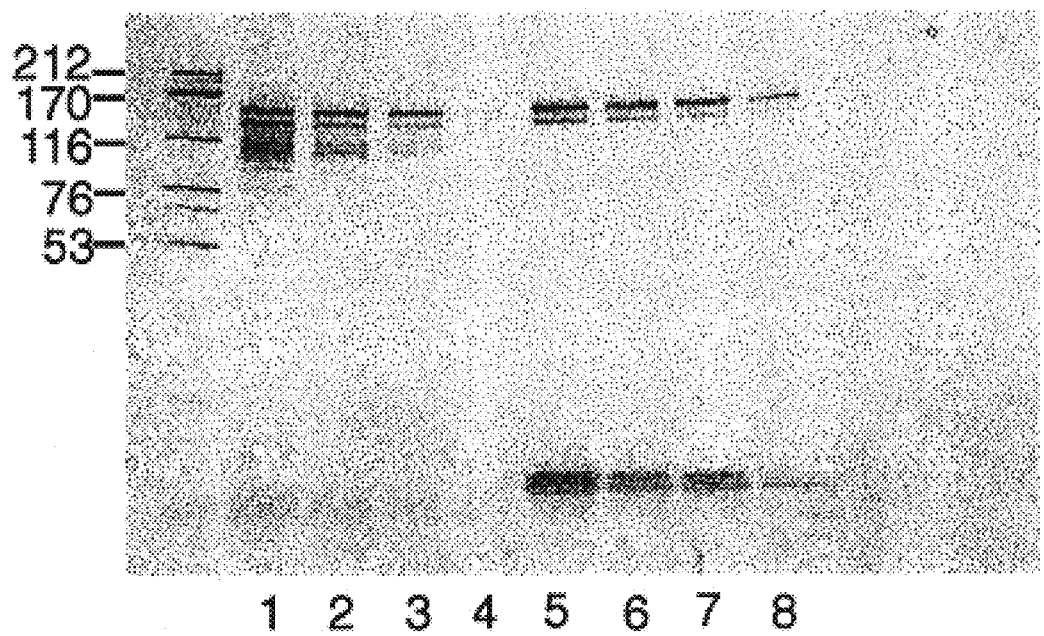
FIG. 1—Comparison of material isolated from conditioned media of human rhabdomyosarcoma cell line A204 and Sigma® human collagen V on a silver stained, reducing 4–20% SDS PAGE. Lanes 1–4: 0.5 $\mu$l, 0.25 $\mu$l, 0.1 $\mu$l and 0.05 $\mu$l loadings of material isolated from A204 conditioned media. Lanes 5–8: 1.0 μg, 0.5 μg, 0.2 μg and 0.1 μg loadings of Sigma® human collagen type V.

The present invention provides for assay systems and methods that may be used to detect and/or measure collagen activity or to identify agents that exhibit collagen activity. The term "collagen activity," as used herein, refers to the activity of collagen, or of other, hitherto unidentified molecules, including peptide and non-peptide molecules, which are capable of binding to Tyro-10 (DDR-2) or NEP (DDR-1).

Accordingly, the present invention provides for a method of detecting or measuring collagen activity comprising (i) exposing a cell that expresses Tyro-10 (DDR-2) or NEP (DDR-1) to a test agent; and (ii) detecting or measuring the specific binding of the test agent to Tyro-10 (DDR-2) or NEP (DDR-1), in which specific binding to Tyro-10 (DDR-2) or NEP (DDR-1) positively correlates with collagen activity.

A cell that expresses Tyro-10 (DDR-2) or NEP (DDR-1) may either naturally express Tyro-10 (DDR-2) or NEP (DDR-1) or be genetically engineered to do so. For example, Tyro-10 (DDR-2) or NEP (DDR-1)-encoding nucleic acid sequences may be introduced into a cell by transfection, transduction, microinjection, electroporation, via a transgenic animal, etc., using any method known in the art.

The specific binding of test agent to Tyro-10 (DDR-2) or NEP (DDR-1) may be measured in a number of ways. For example, the actual binding of test agent to cells expressing Tyro-10 (DDR-2) or NEP (DDR-1) may be detected or measured, by detecting or measuring (i) test agent bound to the surface of intact cells; (ii) test agent cross-linked to Tyro-10 (DDR-2) or NEP (DDR-1) protein in cell lysates; or (iii) test agent bound to Tyro-10 (DDR-2) or NEP (DDR-1) in vitro. The specific interaction between test agent and Tyro-10 (DDR-2) or NEP (DDR-1) may be evaluated by using reagents that demonstrate the unique properties of that interaction.

As a specific, nonlimiting example, the methods of the invention may be used as follows. Consider a case in which the collagen level (or the level of another molecule capable of binding Tyro-10 (DDR-2) or NEP (DDR-1)) in a sample is to be measured. Varying dilutions of the sample, in parallel with a negative control (NC) containing no collagen activity, and a positive control (PC) containing a known amount of collagen, may be exposed to cells that express Tyro-10 (DDR-2) or NEP (DDR-1) in the presence of detectably labeled collagen (for example, radioiodinated collagen). The amount of collagen in the test sample may be evaluated by determining the amount of $^{125}$I-labeled collagen that binds to the controls and in each of the dilutions, and comparing the sample values to a standard curve. The more collagen in the sample, the less $^{125}$I-collagen that will bind to Tyro-10 (DDR-2) or NEP (DDR-1). The amount of $^{125}$I-collagen bound may be determined by measuring the amount of radioactivity per cell, or by cross-linking the collagen to cell surface proteins and detecting the amount of labeled protein in cell extracts, using, for example, SDS polyacrylamide gel electrophoresis, which may reveal a labeled protein having a size corresponding to collagen-bound Tyro-10 (DDR-2) or NEP (DDR-1).

Detectably labeled collagen includes, but is not limited to, collagen linked covalently or noncovalently to a radioactive substance, a fluorescent substance, a substance that has enzymatic activity, a substance that may serve as a substrate for an enzyme (enzymes and substrates associated with colorimetrically detectable reactions are preferred) or to a substance that can be recognized by an antibody molecule that is preferably a detectably labeled antibody molecule.

Alternatively, the specific binding of a test agent to Tyro-10 (DDR-2) or NEP (DDR-1) may be measured by evaluating the secondary biological effects of collagen/Tyro-10 (DDR-2) or collagen/NEP (DDR-1) binding.

Similarly, the present invention provides for a method of identifying an agent that has collagen activity comprising (i) exposing a cell that expresses Tyro-10 (DDR-2) or NEP (DDR-1) to a test agent and (ii) detecting the specific binding of the test agent to Tyro-10 (DDR-2) or NEP (DDR-1), in which specific binding to Tyro-10 (DDR-2) or NEP (DDR-1) positively correlates with collagen activity. Specific binding may be detected by either assaying for direct binding or the secondary biological effects of binding. Such a method may be particularly useful in screening a large array of peptide and non-peptide agents (e.g., peptidomimetics) for collagen activity. In a preferred, specific, nonlimiting embodiment of the invention, a large grid of culture wells may be prepared that contain, in alternate rows, cells that are either Tyro-10 (DDR-2) or NEP (DDR-1)-minus or engineered to be Tyro-10 (DDR-2) or NEP (DDR-1)-plus. A variety of test agents may then be added such that each column of the grid, or a portion thereof, contains a different test agent. Each well could then be scored for the presence or absence of the secondary biological effect. An extremely large number of test agents could be screened for collagen activity in this manner.

In additional embodiments, the invention provides for methods of detecting or measuring collagen activity or identifying an agent as having collagen activity comprising (i) exposing a test agent to a Tyro-10 (DDR-2) or NEP (DDR-1) protein in vitro under conditions that permit binding to occur and (ii) detecting binding of the test agent to the Tyro-10 (DDR-2) or NEP (DDR-1) protein, in which binding of test agent to Tyro-10 (DDR-2) or NEP (DDR-1) correlates with collagen activity. According to such methods, the Tyro-10 (DDR-2) or NEP (DDR-1) may or may not be substantially purified, may be affixed to a solid support (e.g. as an affinity column or as an ELISA assay), or may be incorporated into an artificial membrane. Binding of test agent to Tyro-10 (DDR-2) or NEP (DDR-1) may be evaluated by any method known in the art. In preferred embodiments, the binding of test agent may be detected or measured by evaluating its ability to compete with detectably labeled known Tyro-10 (DDR-2) or NEP (DDR-1) ligands for Tyro-10 (DDR-2) or NEP (DDR-1) binding.

The present invention also provides for a method of detecting the ability of a test agent compound to function as an antagonist of collagen activity comprising detecting the ability of the compound to inhibit an effect of collagen binding to Tyro-10 (DDR-2) or NEP (DDR-1) on a cell that expresses Tyro-10 (DDR-2) or NEP (DDR-1). Such an antagonist may or may not interfere with Tyro-10 (DDR-2)/collagen or NEP (DDR-1)/collagen binding. Effects of collagen binding to Tyro-10 (DDR-2) or NEP (DDR-1) are preferably biological or biochemical effects, including, but not limited to, phosphorylation.

The present invention also provides for collagen mimetics that act as antagonists. Mimetics may be obtained by screening or be designed based upon structural analysis of the binding sites.

The present invention also provides for assay systems that may be used according to the methods described. Such assay systems may comprise in vitro preparations of Tyro-10 (DDR-2) or NEP (DDR-1), e.g. affixed to a solid support, or may, preferably, comprise cells that express Tyro-10 (DDR-2) or NEP (DDR-1) protein.

Cells that express Tyro-10 (DDR-2) or NEP (DDR-1) protein may do so naturally or may be genetically engineered to produce Tyro-10 (DDR-2) or NEP (DDR-1), as described, by transfection, transduction, electroporation, microinjection, via a transgenic animal, etc. of nucleic acid encoding Tyro-10 (DDR-2) or NEP (DDR-1) in a suitable expression vector.

Any of the methods known to one skilled in the art for the insertion of DNA fragments into a vector may be used to construct expression vectors encoding Tyro-10 (DDR-2) or NEP (DDR-1) containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding Tyro-10 (DDR-2) or NEP (DDR-1) protein or peptide fragment may be regulated by a second nucleic acid sequence so that Tyro-10 (DDR-2) or NEP (DDR-1) protein or peptide is expressed in a host transformed with the recombinant DNA molecule.

For example, expression of Tyro-10 (DDR-2) or NEP (DDR-1) may be controlled by any promoter/enhancer element known in the art. Promoters which may be used to control Tyro-10 (DDR-2) or NEP (DDR-1) expression include, but are not limited to the long terminal repeat as described in Squinto et al., (1991, Cell 65:1–20); the SV40 early promoter region (Bernoist and Chambon, 1981, Nature 290:304–310), the CMV promoter, the M-MuLV 5' terminal repeat the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothioein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; promoter elements from yeast or other fungi such as the Gal 4 promoter, the ADH (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing Tyro-10 (DDR-2) or NEP (DDR-1) gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA—DNA hybridization using probes comprising sequences that are homologous to an inserted Tyro-10 (DDR-2) or NEP (DDR-1) gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the Tyro-10 (DDR-2) or NEP (DDR-1) gene is inserted within the marker gene sequence of the vector, recombinants containing the Tyro-10 (DDR-2) or NEP (DDR-1) insert can be identified by the absence of the marker gene function. In the third approach, recombinant expression vectors can be identified by assaying the foreign gene product expressed by the recombinant. Such assays can be based, for example, on the physical or functional properties of the Tyro-10 (DDR-2) or NEP (DDR-1) gene product, for example, by binding of the receptor to collagen or to an antibody which directly recognizes the Tyro-10 (DDR-2) or NEP (DDR-1). Cells of the present invention may transiently or, preferably, constitutively and permanently express Tyro-10 (DDR-2) or NEP (DDR-1).

In preferred embodiments, the present invention provides for cells that express Tyro-10 (DDR-2) or NEP (DDR-1) and that also contain recombinant nucleic acid comprising an immediate early gene promoter (e.g. the fos or jun promoters (Gilman et al., 1986, Mol. Cell. Biol. 6:4305–4316). When such a cell is exposed to collagen, the collagen may be expected to bind to Tyro-10 (DDR-2) or NEP (DDR-1) and secondarily induce transcription of the immediate early promoter. Such a cell may be used to detect collagen/Tyro-10 (DDR-2) or collagen/NEP (DDR-1) binding by measuring the transcriptional activity of the immediate early gene promoter, for example, by nuclear run-off analysis, Northern blot analysis, or by measuring levels of a gene controlled by the promoter. The immediate early promoter may be used to control the expression of fos or jun or any detectable gene product, including, but not limited to, any of the known reporter genes, such as a gene that confers hygromycin resistance (Murphy and Efstratiadis, 1987, Proc. Natl. Acad. Sci. U.S.A. 84:8277–8281) chloramphenicol acetyltransferase (CAT), neomycin phosphotransferase (neo), beta-galactosidase beta-glucuronidase, beta-galactosidase, etc. In a specific embodiment, collagen/Tyro-10 (DDR-2) or collagen/NEP (DDR-1) binding in a cell that expresses Tyro-10 (DDR-2) or NEP (DDR-1) and contains the human growth hormone gene under the control of the fos gene promoter may be expected to produce recombinant human growth hormone, as measured by Seldon et al., 1986, Mol. Cell. Biol. 6:3173–3179. In another embodiment, Tyro-10 (DDR-2) or NEP (DDR-1) expression may also be used as a reporter gene and be placed under the control of an immediate early promoter in addition to constitutively expressed Tyro-10 (DDR-2) or NEP (DDR-1) to produce an amplified response to collagen. Such Tyro-10 (DDR-2)- or NEP (DDR-1)-expression reporter gene containing cell lines may provide an exceptionally sensitive and efficient method of detecting or measuring collagen activity.

The utilization of assay systems comprising the Tyro-10 (DDR-2) and NEP (DDR-1) receptors has led to the discovery, as described herein, that collagen is a cognate ligand for these receptors. Based upon this discovery, applicants have devised a method of screening for a molecule capable of competing with collagen for binding to the extracellular domain of a Tyro-10 (DDR-2) or NEP (DDR-1) receptor comprising:

a) contacting a sample suspected of containing the molecule with the extracellular domain of a Tyro-10 (DDR-2) or NEP (DDR-1) receptor in the presence of collagen under conditions in which the collagen is capable of binding to the extracellular domain; and b) detecting binding of the molecule to the Tyro-10 (DDR-2) or NEP (DDR-1) receptor extracellular domain.

In a preferred embodiment, the collagen is bound to a solid support. In other preferred embodiments, the extracellular domain (including a molecule containing the extracellular domain such as, for example, a receptorbody or the receptor itself) is detectably labeled and includes, but is not limited to, extracellular domain linked covalently or noncovalently to a radioactive substance, a fluorescent substance, a substance that has enzymatic activity, a substance that may serve as a substrate for an enzyme (enzymes and substrates associated with colorimetrically detectable reactions are preferred) or to a substance that can be recognized by an antibody molecule that is preferably a detectably labeled antibody molecule.

The invention thus provides for both a method of identifying molecules capable of neutralizing the ligand or blocking binding to the receptor, as well as the molecules identified by the method. By way of nonlimiting example, the method may be performed via an assay which is conceptually similar to an ELISA assay. For example, collagen may be bound to a solid support, such as a plastic multiwell plate. As a control, a known amount of a molecule which contains the Tyro-10 (DDR-2) or NEP (DDR-1) extracellular domain and which has been Myc-tagged may then be introduced to the well and any tagged molecules which bind the collagen may then be identified by means of a reporter antibody directed against the Myc-tag. This assay system may then be used to screen test samples for molecules which are capable of i) binding to the tagged molecule or ii) binding to the collagen and thereby blocking binding to the collagen by the tagged molecule. For example, a test sample containing a putative molecule of interest together with a known amount of a tagged molecule which contains the Tyro-10 (DDR-2) or NEP (DDR-1) extracellular domain may be introduced to the well and the amount of tagged molecule which binds to the collagen may be measured. By comparing the amount of bound tagged molecule in the test well to the amount in the control well, samples containing molecules which are capable of blocking tagged molecule binding to the collagen may be identified. The molecules of interest thus identified may be isolated using methods well known to one of skill in the art.

Once a blocker of collagen binding is found, one of skill in the art would know to perform secondary assays to determine whether the blocker is binding to the tagged molecule or to the collagen, as well as assays to determine if the blocker molecule can neutralize the biological activity of the collagen. For example, by using a binding assay which employs BIAcore biosensor technology (or the equivalent), in which either 1) the molecule which contains the Tyro-10 (DDR-2) or NEP (DDR-1) extracellular domain, or 2) the collagen, is covalently attached to a solid support (e.g. carboxymethyl dextran on a gold surface), one of skill in the art would be able to determine if the blocker molecule is binding specifically to the extracellular domain containing molecule or to the collagen. To determine if the blocker molecule can neutralize biological activity, one of skill in the art could perform a phosphorylation assay or alternatively, a functional bioassay, such as a survival assay. Alternatively, a blocker molecule which binds to the extracellular domain could be an agonist and one of skill in the art would know to how to determine this by performing an appropriate assay for identifying additional agonists of the receptors.

In another embodiment, the present invention provides a method of screening for a molecule capable of competing with collagen for binding to the extracellular domain of a Tyro-10 (DDR-2) or NEP (DDR-1) receptor comprising:

a) contacting a known amount of the extracellular domain of a Tyro-10 (DDR-2) or NEP (DDR-1) receptor to collagen under conditions in which the collagen is capable of binding to the extracellular domain;

b) determining the amount of the extracellular domain that binds to the collagen;

c) contacting a known amount of the extracellular domain of a Tyro-10 (DDR-2) or NEP (DDR-1) receptor to collagen, in the presence of a sample suspected of containing the molecule capable of competing with collagen, under conditions in which the collagen is capable of binding to the extracellular domain;

d) determining the amount of the extracellular domain that binds to the collagen;

e) comparing the amount from (b) with the amount from (d), wherein a lesser amount in (d) indicates the presence of a molecule capable of competing with collagen for binding to the extracellular domain of a Tyro-10 (DDR-2) or NEP (DDR-1) receptor.

The present invention further provides a method of promoting the growth and/or survival of Tyro-10 (DDR-2) extracellular domain-expressing cells comprising treating the cells with an effective amount of collagen. In one embodiment of the method, said extracellular domain-expressing cells express a chimeric receptor comprising the extracellular domain of Tyro-10 (DDR-2) receptor and the intracellular portion of a receptor tyrosine kinase other than Tyro-10 (DDR-2)

The invention further provides for a method of promoting the growth and/or survival of NEP (DDR-1) extracellular domain-expressing cells comprising treating the cells with an effective amount of collagen. In one embodiment of the method, the extracellular domain-expressing cells express a chimeric receptor comprising the extracellular domain of NEP (DDR-1) receptor and the intracellular portion of a receptor tyrosine kinase other than NEP (DDR-1).

Experimental Procedures

Unless otherwise indicated, the procedures described herein were performed as follows:

Cell Culture and Production of Media

The cell lines used as well as the culture conditions used to prepare conditioned media have previously been described (Davis et al., 1994; Davis et al., 1996; Stitt et al., 1995; Maisonpierre et al., 1997).

Production and Purification of Receptorbodies (Rbodies)

Expression plasmids encoding the ectodomains of DDR1 and DDR2 fused to the hinge, C2 and C3 regions of human IgG1 via a bridging sequence (glycine-proline-glycine) were engineered as previously described for TrkB, Ehk1 and B61 (Davis et al., 1994). The Rbodies encoded by these plasmids were produced according to standard protocols (O'Reilly et al., 1992) in *Spodoptera frugiperda* Sf-21AE cells infected with baculovirus vectors bearing the respective fusion constructs. Recombinant fusion protein were then purified by protein A-sepharose (Pharmacia) chromatography.

Screening for Rbody binding to Cell Surfaces

Cells were plated in 6 or 24 well plates at least 48 hrs before the assay. After the cells were confluent, medium from the cells was removed and replaced with a 2 microgram/ml solution of the Rbody in phosphate buffered saline (PBS) with 10% bovine calf serum (BCS). One hour later the Rbody solution was removed, cells were washed 3 times in PBS/10% BCS, and cells were then incubated with 125-I radiolabelled secondary antibody (from NEN/Dupont) in PBS/10% BCS. Finally cells were washed 3 times in PBS/10% BCS, solubilized in 0.1M NaOH, and bound radioactivity quantitated.

Rbody Slot-Blot Assay

Slot-blots were performed on 0.45u nitrocellulose (S&S) or Nylon membranes. Membranes were pre-wetted with PBS (containing $Ca^{2+}$ and $Mg^{2+}$) and placed on prewetted filter paper. Samples were loaded into wells and drawn through by vacuum. Blots were blocked in a solution of 5% bovine calf serum and 5% non-fat milk in TBS-T (Tris-buffered saline, 25 mM TRIS-HCl, 150 mM NaCl, 0.1% TWEEN20, pH 7.4) for one hour at room temperature or 12 hrs. at 4°°C. overnight. Blots were washed 3×5 min. with TBS-T and then incubated at room temperature for one hour in 2.5 ug/ml solution of receptor-body in 2.5% BCS-2.5% NFM/TBS-T. Blots were washed 3×5min. with TBS-T and then incubated for one hour at room temperature with a 1:5000 dilution of goat anti-human IgG (Fc-sp) antibody HRPO conjugate (Caltag, #10007) in 2.5% BCS-2.5% NFM/TBS-T. Blots were washed 3×5 min. with TBS-T and 2×5 min. with PBS. Blots were developed using ECL detection system (Amersham) and exposed on film (Kodak Scientific Imaging Film XAR-5) for 1–2 minute exposures. As a control, duplicate blots were incubated with unrelated receptor-bodies for which positive controls were available, such as TRKB-Fc detecting BDNF.

Collagenase and Collagen Inhibitor Treatments

Cells were treated with collagenase (clostridiopeptidase A, type VII, from Sigma, Inc.) at 200 U/ml in PBS for 1 hour at 37 C. Conditioned media was treated with collagenase, pepsin and trypsin by incubating a 1.5 ml aliquot of media at 37 C for 5 hours with 5000 IU/ml of collagenase and then stopping the reaction by addition of EDTA to the final concentration of 10 mM; by adjusting the pH of 1.5 ml of conditioned medium to pH 2.5 with acetic acid and incubating overnight at 4 C with 67 IU/ml of pepsin and then stopping the reaction by adjusting pH to 7.4 with NaOH; by adjusting a 1.5 ml aliquot of conditioned medium to 1.0 M Tris, pH 8.2 and 50 mM EDTA, incubating with Trypsin at 2.5 ug/ml at room temperature for 5 hours and inactivating the trypsin by addition of PMSF to 2 mM. For the collagen synthesis inhibitor studies, A204 cells were grown to confluence and then switched to defined medium containing 50 ug/ml of cis-hydroxy-proline and 400 uM ethyl3,4-dihydroxybenzoate and kept in tissue culture for up to 3 days.

Purification of DDR binding activity from A204 condition media 1 liter of A204 serum-free conditioned media was loaded at neutral pH (7.4) onto a 10 ml HiTrap S cation exchange column and the activity was eluted with 200 ml of a 0.15–1.0 M NaCl gradient. Positive fractions were identified using the DDR Rbody slot blot assay. Activity was precipitated from the pool of active fractions with 20 mM calcium chloride. The precipitate was taken up in 40 mM EDTA and dialyzed overnight against 0.5 M acetic acid containing 0.15 M NaCl. Pepsin was added to the solution to the final concentration of 50 IU/ml (20 ug/ml) and the sample was incubated at 4° C. for 24 hours. Sodium chloride concentration in the sample was adjusted to 1.2 M. The resulting precipitate was recovered after high speed centrifugation and dissolved in 40 mM Tris HCl buffer pH 8, containing 1 M NaCl. Proteins were again precipitated with 4.5 M NaCl. The precipitate was redissolved in 40 mM Tris HCl containing 1 M NaCl and injected onto 3.2×30 Pharmacia Superose 6 PC column equilibrated at 4° C. in 40 mM Tris HCl buffer containing 150 mM NaCl and 6 M urea. The column was run at 0.04 ml/min using Pharmacia Smart System. The effluent was monitored at 230 nm wavelength. The purification process afforded about 0.3 mg of total protein. Fractions from the column were applied directly onto a 0.45 um nitrocellulose membrane. Fractions that eluted near the exclusion volume of the column showed the most intense staining in the receptor binding slot blot. Those fractions were pooled and an aliquot was dialyzed against 40 mM Tris HCl, 1 M NaCl buffer and used in the DDR receptor autophosphorylation assay. Another aliquot was dialyzed extensively against 12 mM HCl and used for a quantitative amino acid analysis.

Purification of Commercially-Derived Collagen V 2 mg of human placental collagen type V (Sigma, Inc.) was dissolved in 25 mM Tris HCl, pH 8.2 containing 50 mM NaCl and 2M urea, and loaded onto a 5 ml Fractogel EMD SO3 strong cation exchange column. The column was eluted at room temperature with 200 ml of a 0–1.0 M NaCl gradient at 2 ml/min. Fractions were pooled based on the receptor slot-blot activity and their purity was analyzed by SDS gel electrophoresis on 4–20% polyacrylamide gels. Activity eluted between 0.4 and 0.5 M NaCl. Active fractions were pooled, dialyzed to reduce NaCl concentration and injected onto a Pharmacia 1.6×5 MonoS PC cation exchange column. The protein was eluted from the column with a sharp gradient of NaCl in a final volume of 0.08 ml. The sample was then run at 4° C. on a 3.2×30 Superose 6 PC gel filtration column equilibrated in 40 mM Tris HCl pH 8.2 buffer containing 6 M urea. Sample was dialyzed against 40 mM Tris HCl, 1 M NaCl buffer for use in the DDR receptor phosphorylation assay.

Direct Red Assay for Collagen Quantitation

Slot-blots or dot-blots were prepared as for Rbody blotting procedure. Blots were either first blotted with Rbody or directly transferred to a 0.1% solution of Direct Red (Sirius Red) dye in saturated picric acid and incubated for 12 hrs at room temperature. Blots were washed with 10 mM HCl until washes showed no yellow color. Blots were washed with Mili-Q water and allowed to air dry. Intensity and location of collagen containing samples were noted qualitatively or spots were cut out of membrane, placed in a microfuge tube containing 100 ul of 100 mM NaOH, vortexed occasionally over 30 min. and the absorbance at 570 nm of the colored extract determined. Absorbances of extracts from samples were compared to those from a standard curve of blotted Vitrogen 100 in a range from 0–10 ug Vitrogen 100/well.

Protein Assays

To samples plus enough Mili-Q water to make 0.9 ml was added 0.1 ml. BIO-RAD protein assay dye reagent concentrate. Samples were vortexed on addition of dye reagent and allowed to stand at room temperature for 10–20 min. Absorbances at 595 nm was read and compared to standard curves of 0–20 ug/assay bovine serum albumin or Vitrogen 100. Standard curves were found to coincide for protein concentrations up to 10 ug/assay after which response of Vitrogen100 decreases.

Tyrosine Phosphorylation Assays

COS cells were plated 24 hours before transfection in 10 cm tissue culture plates at 106 cells/plate, then transfected with 5 micrograms of pCMX-DDR1-myc3 construct using a DEAE transfection protocol as described (Davis et al., 1994), and maintained in 10% BCS/DMEM after transfection. The pCMX-Nep-myc3 construct encodes a full length DDR1 receptor fused to three consecutive myc epitope tags at its carboxyterminus. Two days after transfection, the cell media was removed and replaced with DMEM lacking serum. The next day the serum-starved cells were stimulated for 1 hour at 37° C. with collagens by adding 0.1 ml of appropriate amounts of collagen in 1% acetic acid; for controls, 1% acetic acid lacking collagen was added. At various times after collagen challenge, the cells were lysed in 1% NP40 in PBS containing 1 mM PMSF, 0.14 U/ml aprotinin, 1 mM EDTA, and 1 mM sodium orthovanadate. The lysates were immunoprecipitated with lectin from Triticum Vulgaris conjugated with agarose macrobeads (Sigma, Inc.) and immunoblotted with the phosphotyrosine-specific monoclonal antibody 4G10 (1:5000, Upstate Biotechnology, Inc.). In each case, the blots were stripped with glycine strip buffer and subsequently immunoblotted with the myc-specific 9E10 antibody to control for DDR1 receptor levels. Immobilized collagen-coated plates for phosphorylation assays were created by soaking plates in 0.5% acetic acid for 20 minutes at 60° C., rinsing with distilled water, and incubating with 0.1 mg/ml of collagen solution in 0.1M acetic acid overnight at room temperature. The next day the plates were washed with DMEM and dispersed cells (the serum-starved cells prepared as above but removed from plates via trypsin treatment) were added for the phosphorylation assays.

EXAMPLE 1

Screening for Receptor-Binding Activity

The Tyro-10 (DDR-2) and NEP (DDR-1) receptors each have a unique discoidin domain as part of their ecto-domain and a kinase domain similar to the Trk family of kinases. In order to assay for receptor binding activities, chimeric constructs expressing Tyro-10 (DDR-2) and NEP (DDR-1) receptor bodies (ecto-domains of these proteins individually fused to Fc portion of human IgG1) were made. A method of preparing receptorbodies is described in Goodwin, et. al., Cell 73: 447–456 (1993). Radioiodinated receptorbodies were then used to screen approximately 200 cell lines, as well as defined media from those cell lines, to look for cell surface binding activities and secreted activities. Screening identified the cell lines A204 (rhabdomyosarcoma), U373MG (glioblastoma), Saos2 (Sarcoma) and Hela (epithelioid carcinoma) as having the best binding activity for Tyro-10 (DDR-2) and NEP (DDR-1). Interestingly A204 cells also secreted the binding activity into the media, as determined by slot blot.

It was also observed that Tyro-10 (DDR-2) receptorbody appeared to bind to G8 (myoblast) cells when the cells were plated on a collagen coated plate but not when the cells were plated on a non-coated plate. Binding of the receptors was subsequently observed when collagen coated plates without any cells were used for binding assays.

A204 cells, maintained in a DMEM+F12 serum free medium, secreted an activity which could be detected in a receptor slot-blot assay. The activity was specific for Tyro-10 (DDR-2) and NEP (DDR-1) receptors. A204 conditioned media did not show specific binding to Tyro-10 (DDR-2) receptor immobilized on a BIAcore biosensor chip. Similarly, affinity chromatography on a Tyro-10 (DDR-2) receptorbody affinity column did not deplete A204 conditioned media of Tyro-10 (DDR-2) binding activity. Gel filtration chromatography showed that Tyro-10 (DDR-2) binding activity behaved like a very large molecule—it eluted close to the excluded volume on a Superose 6 column. In some experiments though, activity was found also in fractions eluting after the column included volume. This finding was suggestive of an unusual molecular shape associated with the active species. Several attempts to decrease molecular weight of the activity were undertaken—detergents (zwittergen 6–12, digitonin, N-dodecylmaltoside, N-octylglucoside, NP 40, Triton X100, Tween 20, sodium deoxycholate, CHAPS and SDS), chaotropic agents (up to 6 M urea, up to 2 M guanidine hydrochloride), pH between 3 and 11, high salt concentration, reducing agent DTT at 20 mM as well as combination of various treatments did not result in a decrease of the size of the activity. 4 molar and higher guanidinium chloride destroyed the activity.

Tyro 10 binding activity could be precipitated out of A204 conditioned media with 20 mM calcium chloride. 40 mM EDTA released the activity from the precipitate. The activity was retained by the following chromatographic resins—cation exchange at neutral pH, anion exchange at pH 8.5, hydrophobic interaction at 0.7 M ammonium sulfate. The activity could be eluted with specific reagents from those columns with satisfactory recovery of activity. A204 rhabdomyosarcoma line was known to lay down a highly insoluble matrix of alpha 2 chain of collagen XI and alpha 1 chain of collagen V. (Kleman, Jean-Philipe, et al., (1992), Eur. J. Biochem. 210: 329–335). Based on the above observations, we speculated that the Tyro 10 and NEP (DDR-1) binding activity was in fact collagen.

EXAMPLE 2

Purification of Tyro 10 Binding Activity Out of A204 Conditioned Media

Figure 2A:
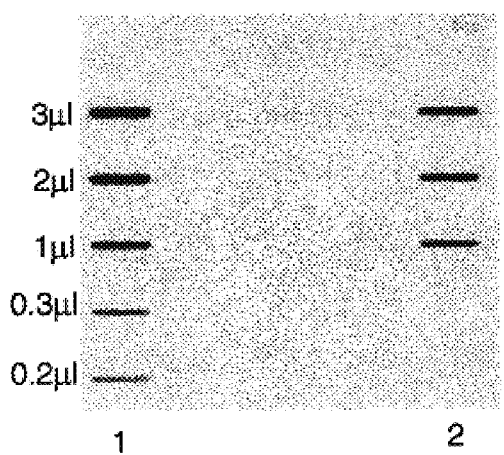
FIGS. 2A & 2B—Receptorbody slot blot of material isolated from conditioned media of A204 cells and commercial (Sigma®) collagen type V.
Figure 2B:
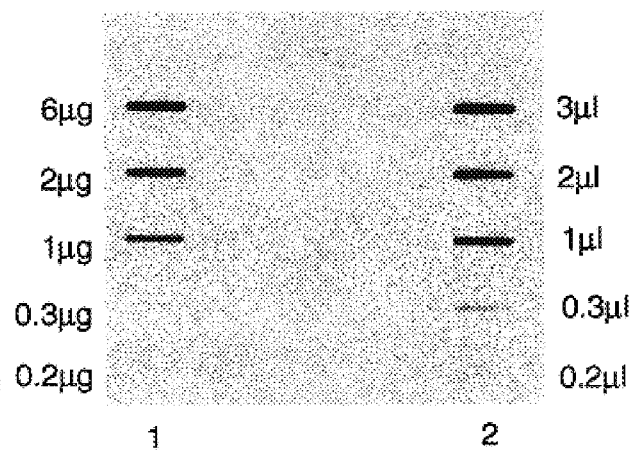
Figure 3A:
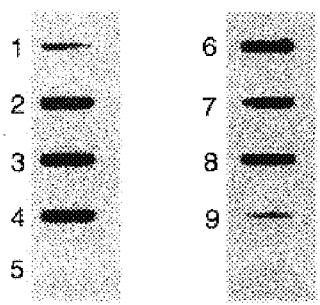
FIGS. 3A to 3C—Slot blot staining assay of commercial collagens with Tyro-10 (DDR-2) (FIG. 3A), NEP (DDR-1) (FIG. 3B) and Trk B (FIG. 3C) receptorbodies. All collagen samples were purchased from Sigma® and assayed at 10 μg loadings. Lane 1—Collagen type I (kangaroo tail); Lane 2—Collagen type II (bovine nasal septum); Lane 3—Collagen type II (bovine tracheal cartilage); Lane 4—Collagen type I (calf skin); lane 5—Collagen type IV (human placenta); Lane 6—Collagen type I (rat tail); Lane 7—Collagen type I (human placenta); Lane 8—Collagen type V (human placenta); Lane 9—Collagen type III (human placenta).
Figure 3B:
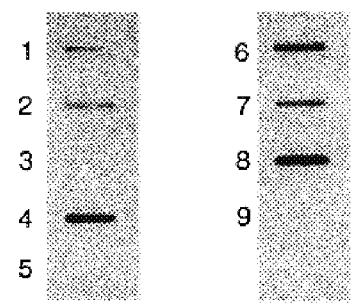
Figure 3C:
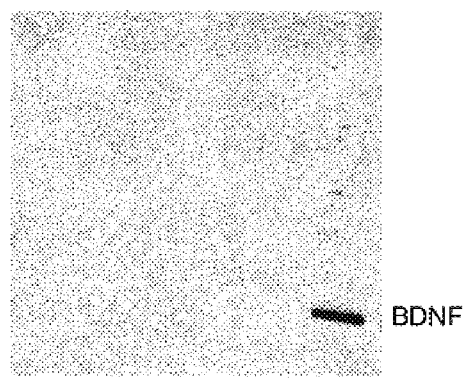

A204 conditioned media was loaded at neutral pH (7.4) onto a cation exchange column and the activity was eluted with NaCl gradient. Positive fractions were identified using receptor slot blot. From the pool of active fractions, activity was precipitated with 20 mM calcium chloride. The precipitate was taken up in 40 mM EDTA and dialyzed overnight against 500 mM acetic acid. Pepsin was added to the solution after the dialysis. The sample of purified material was run on reducing SDS PAGE and compared with commercially available collagens (See FIG. 1). Our sample most closely resembled collagen type V when compared to collagen preparations obtained from Sigma. Pepsin treated sample retained full activity in a slot blot assay in respect to binding of Tyro 10 or NEP (DDR-1) (See FIGS. 2A and 2B). Binding was also observed when collagens were slot-blotted on nitrocellulose membrane (See FIGS. 3A to 3C). When the sample of A204 conditioned media was subjected to collagenase treatment, all Tyro 10 and NEP (DDR-1) binding activity was lost. Binding on each and every cell that scored positive for Tyro-10 (DDR-2) and NEP (DDR-1) activity was also found to be sensitive to collagenase.

A204 cells were cultured in presence of two collagen synthesis inhibitors: cis-hydroxyproline and ethyl dihydroxybenzoate. Tyro 10 staining was not detected in samples from the collagen synthesis inhibition experiment. At the same time, cells untreated with collagen synthesis inhibitors produced Tyro 10 binding activity detectable by slot blot. SDS PACE analysis of the conditioned media produced by inhibitor treated cells demonstrated absence of collagen bands.

EXAMPLE 3

Figure 4A:
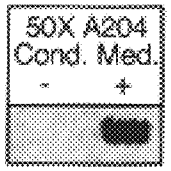
FIGS. 4A & 4B—Phosphorylation of NEP (DDR-1) receptor induced by various sources of collagen.
Figure 4B:
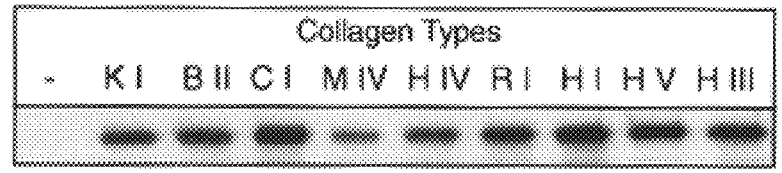

Phosphorylation of NEP (DDR-1) Receptor is Induced by Collagen 1 million COS cells per 10 cm plate were transfected with 5 microgram of a pCMX-NEP (DDR-1)-myc construct using DEAE transfection protocol. Two days after transfection, the media was switched from DMEM containing 10% FBS to serum free DMEM for overnight starvation of cells. After starvation, cells were then stimulated for 1 hr by adding 100 microliter of 1 mg/ml stock solution of collagen in 1% acetic acid (final concentration 10 $\mu$g/ml) as shown in FIG. 4B. In the mock lane (−), 100 microliter of 1% acetic acid was added. After stimulation, the cells were lysed in 1% NP40/1 mM Orthovanadate containing lysis buffer. 200 microliters of this lysate was immunoprecipitated with 40 microliters of Lectin from *Tritium vulgaris* on 6% agarose macrobeads (Sigma®) and analyzed by immunoblotting with anti-p-tyr antibody. The results are shown in FIGS. 4A & 4B. In FIG. 4A, 50× A204 conditioned media was used to stimulate the cells (+) and the mock control (−) was stimulated using unconditioned medium.

To summarize, in order to identify potential source(s) of DDR1 and DDR2 ligand(s), we first engineered plasmids that could be used to express the DDR1 and DDR2 ectodomains individually fused to the Fc portion of human IgG1. We had previously used similar receptor-antibody fusions (termed "Rbodies") to detect and identify ligands for several other receptor tyrosine kinases, including TrkB (to detect its ligands, BDNF and NT4), members of the Eph family (to detect their ligands, collectively referred to as the Ephrins), Tyro3/Sky/rse/brt/tf and Axl/Ark/UFO (to detect their ligands, Protein S and Gas6), MuSK (to detect its ligand, agrin), and Tie1 and Tie2 (to detect their ligands, the angiopoietins) (Davis et al., 1994; Stitt et al., 1995; Glass et al., 1996; Davis et al., 1996; Maisonpierre et al., 1997). These previous studies had assayed Rbodies for their direct binding to cell surfaces to identify cell-associated ligands (e.g. Davis et al., 1994), or used Rbodies to screen conditioned media from cell lines to identify released ligands (e.g. Stitt et al., 1995; Glass et al., 1996; Davis et al., 1996). The latter screens involved either covalently coupling the Rbody to the surface of a BIAcore sensor chip (Johnsson et al., 1991; Fagerstam, 1991) and then using the BIAcore to detect binding activity in conditioned media passed over the surface of this chip, or immobilizing proteins in conditioned media on nitrocellulose membrane slots followed by blotting with the Rbody to detect potential ligands.

Figure 5A:
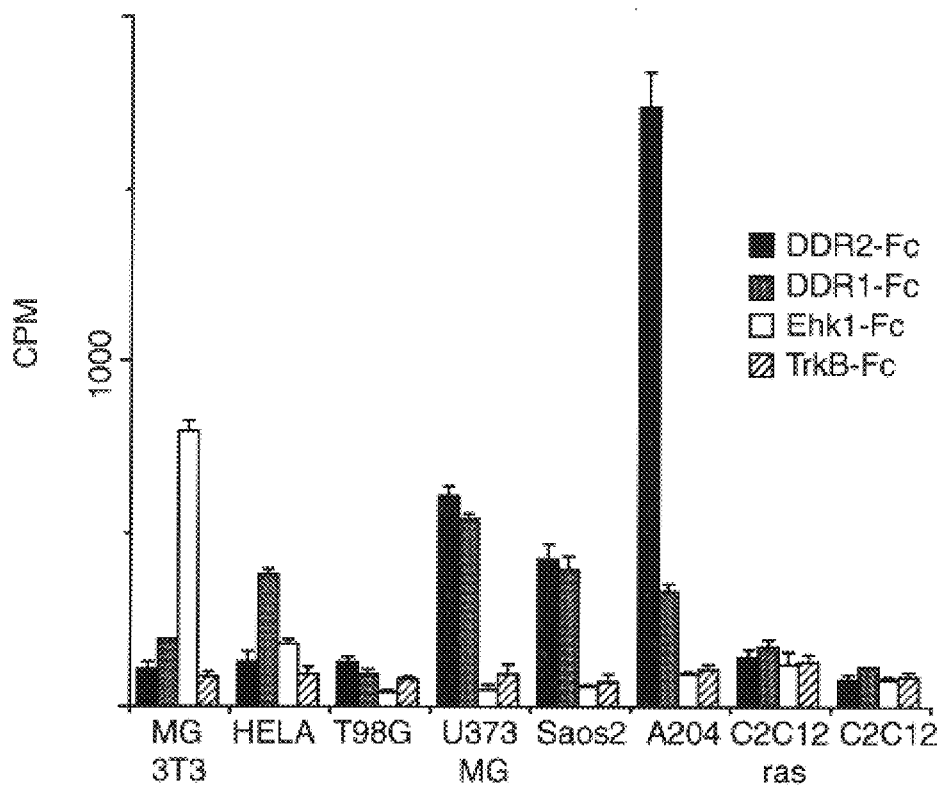
FIGS. 5A–5D—Detection of cell line sources of ligands that bind and activate DDR receptors.
Figure 5B:
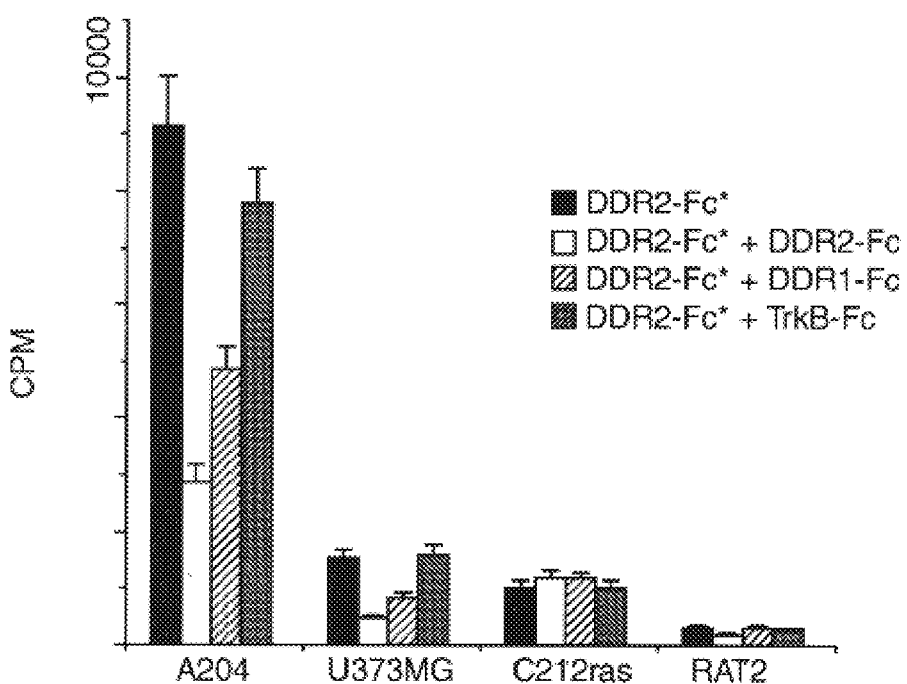

Screening of more than 200 cell lines for cell-associated or released ligands for DDR1 and DDR2, using DDR1 and DDR2 Rbodies, was performed using the three assays described above. While none of the lines revealed binding activity in their conditioned media using the BIAcore assay, cell surface binding assays indicated that four cell lines were specifically bound by both the DDR1 and DDR2 Rbodies, albeit to differing degrees, but not by control Rbodies (FIG. 5A). The four cell lines displaying potential cell-associated ligand activity for both DDR1 and DDR2 included A204 (rhabdomyosarcoma), U373MG (glioblastoma), Saos2 (osteosarcoma) and Hela (epithelioid carcinoma) (FIG. 5A). Cell surface binding assays using I-125 radiolabelled DDR2 Rbody, which could then be assayed for competition by excess levels of the DDR Rbodies as compared to control Rbodies, confirmed the specificity of the binding activity for DDR1 and DDR2, and competition by both DDR1 and DDR2 Rbodies demonstrated that both DDR1 and DDR2 were binding to the same potential ligand on the surfaces of these cells (FIG. 5B).

Figure 5C:
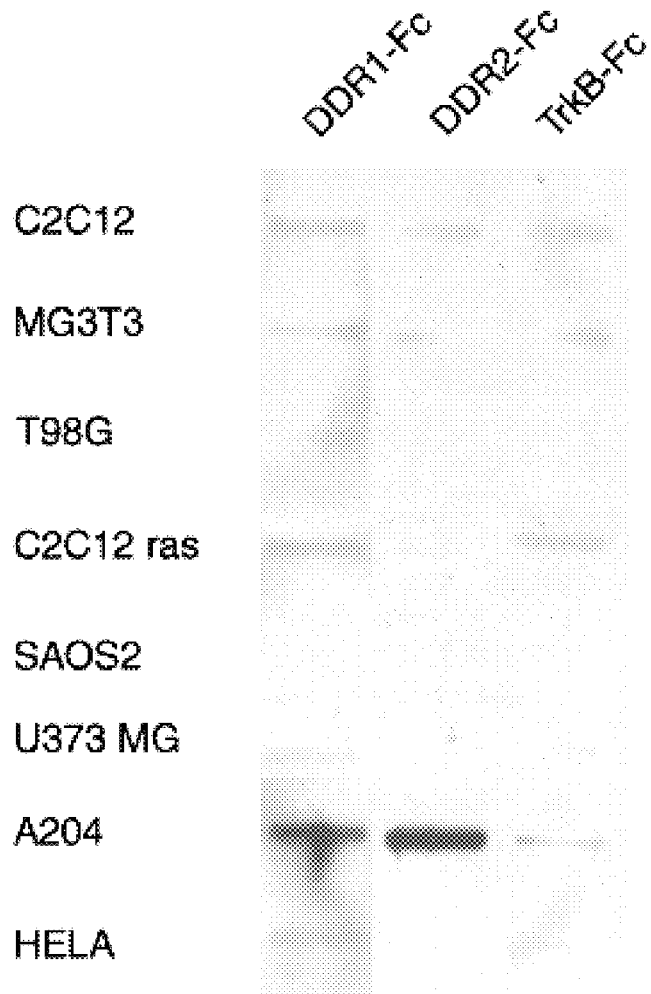

Although, as noted above, none of the cell lines screened detectably released DDR1/DDR2 binding activity as evaluated in the BIAcore assay, the conditioned media of one cell line exhibited binding activity for both DDR1 and DDR2 as evaluated in the nitrocellulose slot-blotting assay (FIG. 5C). This cell line, A204, corresponded to the line exhibiting the maximum cell-associated DDR1/DDR2 binding activity (FIG. 5A), strongly suggesting that the cell-associated and released binding activities of A204 corresponded to the same putative DDR1/DDR2 ligand; consistent with this possibility, a relative preference for DDR2 binding as compared to DDR1 binding was detected for A204 in both the cell surface binding assay and the slot-blotting assay (compare FIGS. 5A and 5C). The ability to detect putative released ligand by slot-blotting versus BIAcore screening is consistent with previous observations that slot-blotting may in some cases provide a more sensitive assay, particularly for low-affinity ligands that may benefit from cooperative binding interactions provided by immobilized ligand being detected by a dimeric Rbody.

Figure 5D:
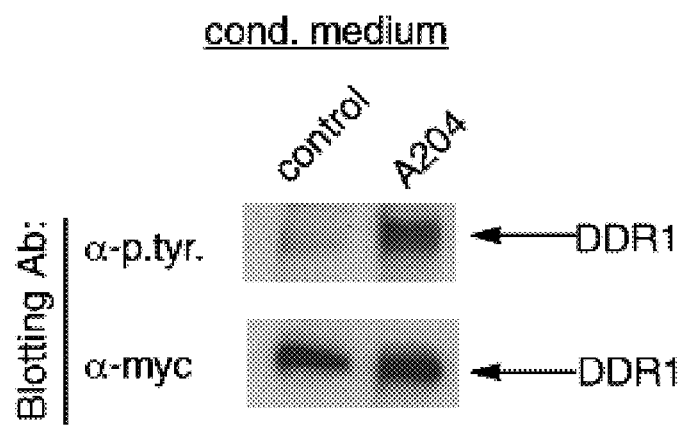

To provide additional support that the binding activities detected by DDR Rbody binding corresponded to bona fide ligands for the DDR receptors, we tested whether they could also activate full-length DDR receptors. For this purpose we engineered a plasmid encoding a full-length DDR1 receptor that was epitope-tagged at its caroboxy-terminus with a triple-myc tag, then used this plasmid to express this epitope-tagged receptor in mammalian cells. These cells were subsequently challenged with either 50-fold concentrated conditioned media from control cells or from the A204 cell line, and then the introduced DDR1 receptors were immunoprecipitated using antibodies against the triple-myc epitope and immunoblotted for phosphotyrosine levels. This analysis demonstrated that the A204 conditioned media, which contains high levels of DDR-binding activity, could induce DDR1 receptor phosphorylation (FIG. 5D), providing further evidence that this DDR-binding activity corresponded to a bona fide ligand for DDR receptors.

EXAMPLE 4

Purification of DDR Binding Activity from A204 Cells Identifies Collagen as a Ligand Biochemical and chromatographic analyses and separations were undertaken to characterize and purify the putative DDR ligand from the conditioned media of A204 cells; binding activity was followed using the slot-blotting assay described. Size exclusion chromatography revealed that DDR binding activity behaved in a manner expected for a very large molecule: under nondenaturing conditions the activity was consistently eluting close to the excluded volume of a Pharmacia Superose 6 column (exclusion limit for globular proteins $4\times10^7$). Several attempts to reduce the molecular weight of the activity were undertaken. We used detergents (zwittergen 6–12, digitonin, N-dodecylmaltoside, N-octylglucoside, NP 40, Triton X100, Tween 20, sodium deoxycholate, CHAPS) chaotropic agents (up to 6 M urea, up to 2 M guanidine hydrochloride), pH between 3 and 11, high salt concentrations, reducing agent DTT and combination of these various treatments; binding activity was always found in the retentates of 100 KD filtration membranes. The activity present in A204 conditioned medium was lost in 4 M guanidine hydrochloride and upon heating to 60° C., was resistant to the action of the nonspecific nuclease Benzonase, but also surprisingly resistant to pepsin and trypsin digestion, suggesting that it might correspond to a protease-resistant protein. DDR binding activity was retained by the following chromatographic resins: cation exchange at neutral pH, anion exchange at pH 8.0, hydrophobic interaction at 0.7 M ammonium sulfate; the activity could be eluted with specific reagents from those resins. We also found that DDR binding activity could be precipitated out of A204 conditioned media with 20 mM calcium chloride, suggesting affinity for calcium phosphate, and then released from the precipitate using 40 mM EDTA. All our observations were consistent with a large protein factor being responsible for the binding, despite the resistance to trypsin and pepsin.

Figure 7A:
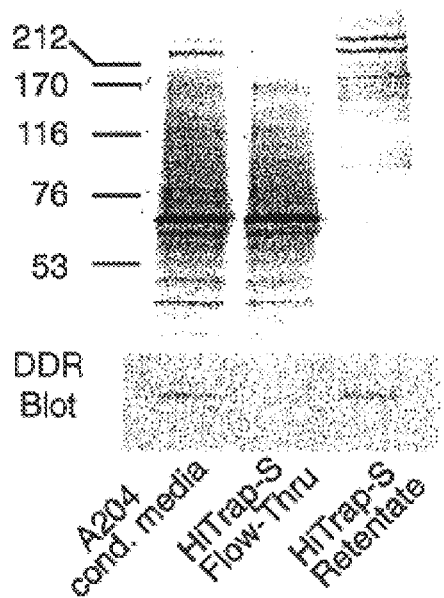
FIG. 7A–7D—Gel Electrophoretic, Slot-Blot, Size Exclusion and Phosphorylation Analysis of A204-derived DDR ligand During Purification Procedure.
Figure 7B:
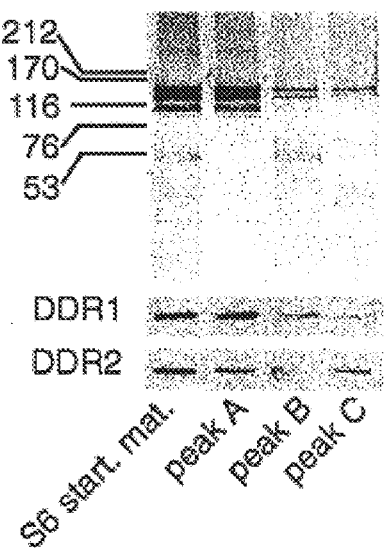
Figure 7C:
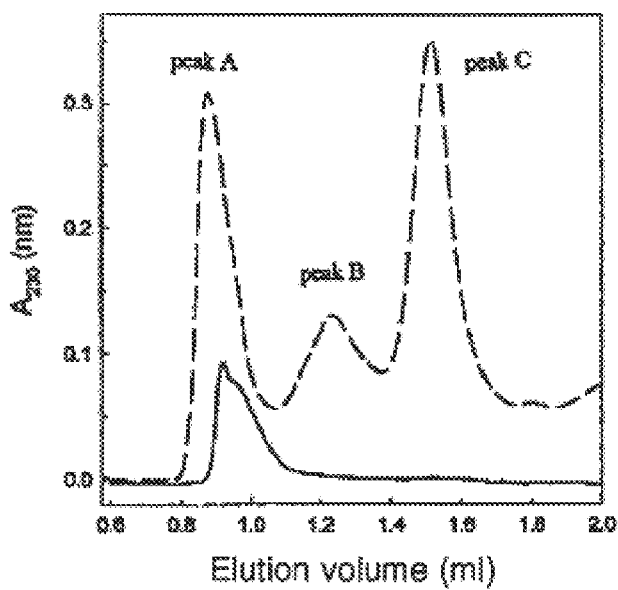
Figure 7D:
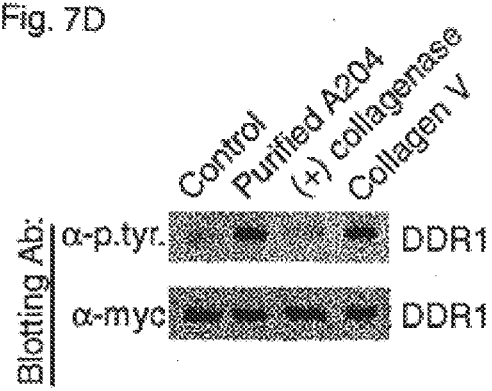

Based on the above biochemical characterizations, we developed a purification procedure to obtain a homogenous binding activity from A204 conditioned medium. The purification protocol consisted of cation exchange chromatography, calcium chloride precipitation, pepsin digestion, high salt precipitation and finally size exclusion chromatography performed in the presence of 6 M urea (FIG. 6A). Silver stained SDS polyacrylamide gel electrophoresis of the final product showed three bands in the region of 150 kD (FIG. 7B, see peak A); the purified protein (after dialysis to remove the urea) was still able to induce phosphorylation of the DDR1 receptor (FIG. 7D, lane 2) and still active in the membrane slot-blot assay (FIG. 7B). Quantitative amino acid analysis on the isolated material revealed that almost a third of the residues were glycine and also demonstrated a high content of hydroxyproline and proline (FIG. 6B), a composition highly characteristic of the triple-helical regions of the collagens.

The collagens consist of a superfamily with about 20 members that are characterized by chains comprised of repeating Gly-X-Y sequences, in which proline is often in the X position while 4-hydroxyproline is often in the Y position, with three collagen "alpha" chains coming together to form a unique triple-helical structure (Prockop, D. J., and Kivirrikko, K. I., 1995, Annu. Rev. Biochem. 65: 403–34). The most abundant collagens can be split into either fibrillar-forming collagens (types I, II, III, V and XI) in which triple helical "monomers" further associate to form large fibrils, or network-forming collagens (types IV, VIII and X) associate to form net-like structures (Prockop, D. J., and Kivirrikko, K. I., 1995, Annu. Rev. Biochem. 65: 403–34). Notably, the fibrillar collagens have long uninterrupted triple-helical regions which are highly resistant to pepsin and trypsin digestion, like the binding activity we isolated from A204 cells. The A204 rhabdomyosarcoma line was previously reported (Kleman, J. -P., et al., 1992, Eur. J. Biochem. 210: 329–335) to produce fibrillar heterotypic trimeric collagen molecules consisting of two alpha 1 chains of collagen XI and one alpha 2 chain of collagen V. In fact, our deduced amino acid composition was indeed even more similar to that predicted for the helical regions of collagen types V and XI than to collagen type I, particularly with respect to the characteristically lower levels of alanine residues (FIG. 6B). Furthermore, assaying for collagen during our purification procedure revealed we had achieved a dramatic enrichment for collagen (FIG. 6A, last column), and the final purified material closely co-migrated with pepsin-treated commercially-derived collagen type V during gel electrophoresis and in size-exclusion chromatography (compare dashed profile, peak A, with solid profile in FIG. 7C). Finally, commercially-derived human collagen type V (Sigma, Inc.) was able to induce phosphorylation of the DDR1 receptor comparable to that of the A204-derived material (compare lanes 2 and 4 in FIG. 7D).

EXAMPLE 5

Further Evidence Indicating that Collagens are DDR Ligands

Figure 8A:
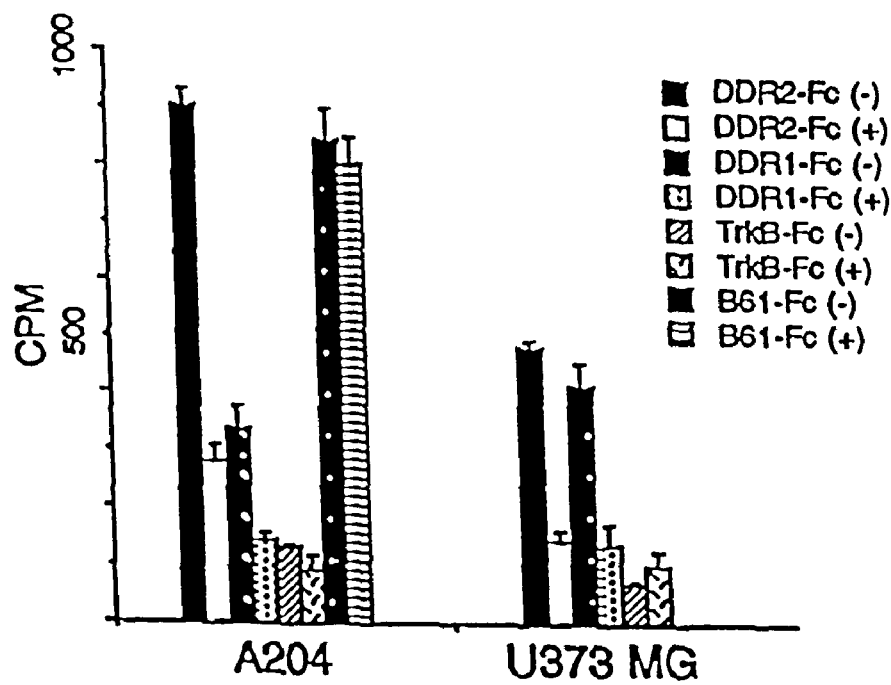
FIG. 8A—Cell-associated DDR binding activity exhibited by A204 and U373 cells is eliminated following treatment with collagenase. Note that U373 exhibits similar levels of binding to both DDR1 and DDR2, which are both reduced by collagenase, while A204 exhibits 2–3-fold more binding to DDR2 than DDR1, although binding of both DDR1 and DDR2 to A204 cells are dramatically reduced by collagenase treatment; different relative binding of DDR1 as compared to DDR2 in the two cell lines probably reflects differences in the types of collagens synthesized by the two cell lines. The binding of B61-Fc to A204 cells serves as a control for a cell surface binding activity that is not reduced by collagenase.
Figure 8B:
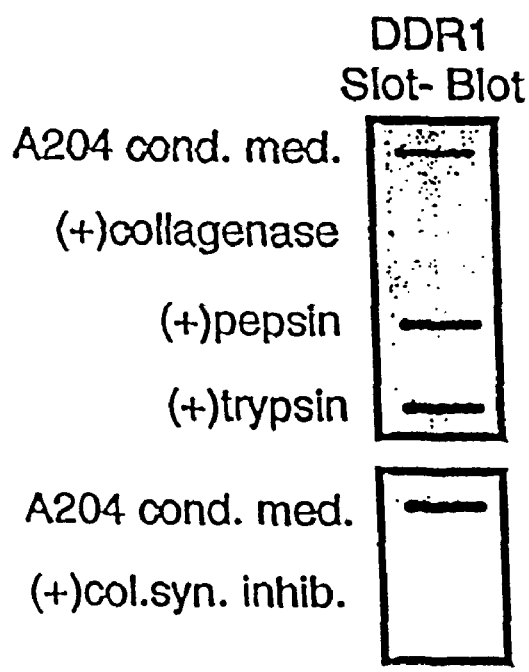
FIG. 8B—DDR1 Slot-Blot assay demonstrating that collagenase treatment or collagen synthesis inhibitors (CHP and EDHB) eliminate the released DDR binding activity normally found in A204 conditioned media.

To confirm that the DDR binding and phosphorylating activity we had been characterizing was indeed collagen, we next examined whether this activity required the production and integrity of collagen. We first evaluated the sensitivity of our DDR binding activity to microbial collagenase type VII (Sigma, Inc.) that can specifically degrade the triple-helical portions of collagens. Collagenase treatment of A204 and U373MG cells, which exhibited cell-associated DDR binding, effectively reduced this binding (FIG. 8A); collagenase treatment did not effect background levels of control TrkB Rbody binding to these cells or that of specific B61-Fc binding to these cells (FIG. 8A). Similarly, collagenase treatment (in contrast to pepsin and trypsin treatment) eliminated the DDR binding activity (FIG. 8B) as well as the DDR phosphorylating activity (FIG. 7D, lane 3) found in A204 conditioned medium. Furthermore, the addition of a cocktail of collagen synthesis inhibitors (cis-hydroxyproline (CHP) and ethyl-3,4-dihydroxybenzoate (EDHB)) to A204 cells prevented their production and release of DDR binding activity (FIG. 8B). Altogether, these data strongly suggest that the DDR binding and phosphorylating activity we had identified in A204 and other cells corresponded to collagen itself.

Figure 9:
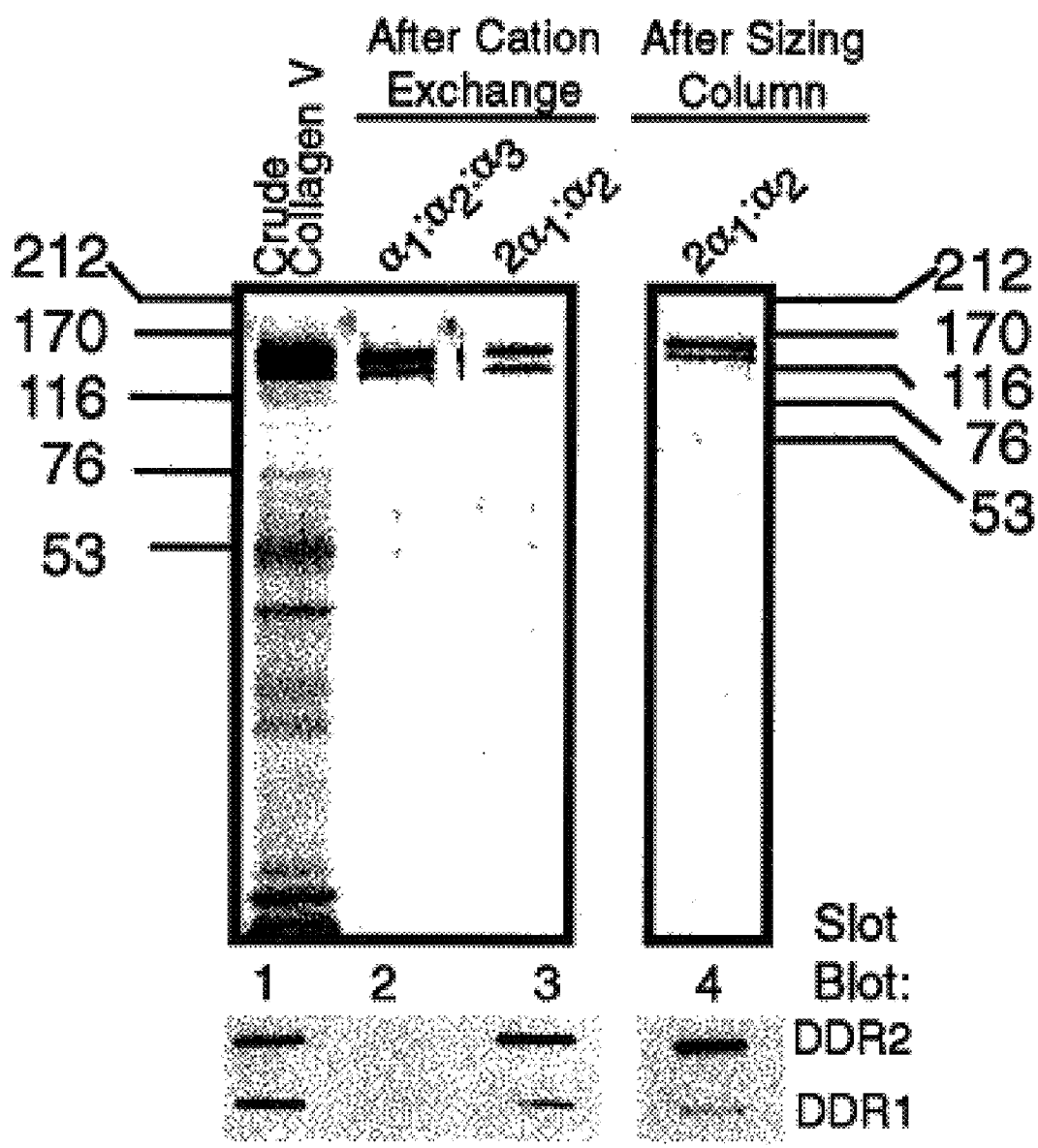
FIG. 9—Gel Electrophoretic and Slot-Blot Analysis of Purification Procedure for commercially-derived (Sigma, Inc.) human placenta collagen type V. SDS PAGE of crude collagen V (lane 1), inactive (consisting of α1: α2: α3, lane 2) and active pools (consisting of 2 α1: α2, lane 3) from Fractogel EMD SO-3 cation exchange column, and active material from Superose 6 sizing column (consisting of 2 α1: α2, lane 4); activity determined by DDR Slot-Blot assays depicted below gels, and also DDR phosphorylation assays (e.g. see FIG. 7D, lane 4).

To further rule out the possibility of a tightly-associated factor, preparations of commercially-derived human collagen type V (Sigma, Inc.) were exploited. These preparations were noted to contain impurities and/or collagen fragments in addition to the intact alpha chains (FIG. 9, lane 1), and thus we developed purification procedures that resulted in the isolation of electrophoretically pure alpha collagen type V (FIG. 9, lane 4). The first purification step was based on a published procedure for purification of crude collagen V (Sato, et al., 1995, Journal of Chromatography B 663: 25–33). The crude preparation was first loaded onto a cation exchange column (Fractogel EMD SO-3) in the presence of 2 M urea. Salt gradient elution resulted in the separation of two trimeric forms of placental collagen V: alpha 1:alpha 2: alpha 3 trimer and (alpha 1)$_2$: alpha 2 trimer. We found that only the (alpha 1)$_2$: alpha2 form of collagen V was active in the DDR slot-blot assay (FIG. 9, lanes 2 and 3). The active heterotrimer was subsequently run on a Pharmacia Superose 6 size exclusion chromatography column. In an attempt to dissociate collagen from any hypothetical components required for DDR binding, chromatography was performed in 6 M urea. After size exclusion chromatography, the collagen chains (alpha 1 and alpha 2 in apparent 2:1 ratio) were the only visible bands on the silver stained 18% polyacrylamide gel (FIG. 9, top, lane 4). The binding (FIG. 9, bottom, lane 5) and phosphorylating activity (following dialysis to remove urea, FIG. 7D, lane 4) was maintained throughout this rather stringent treatment, suggesting that the collagen alone is sufficient for the binding. We could not find any other protein component associated with collagen that would be required for activity. Using anion exchange chromatography (Sato, et al., 1995, Journal of Chromatography B 663: 25–33), we separated individual alpha chains from the active trimer of collagen V. Slot-blot assays showed no activity associated with individual chains, indicating that the three-helical configuration of collagen is required for its DDR activity.

Together with the purification of collagen from A204 conditioned media as the putative DDR ligand, the resistance of this putative DDR ligand to pepsin and trypsin coupled with its sensitivity to collagenase and collagen synthesis inhibitors, as well as the inability to dissociate DDR activity away from collagen using stringent conditions, strongly indicate that collagen corresponds to the DDR ligand we have identified in A204 and other cells. Furthermore, our findings indicate that the native, triple-helical configuration of collagen is required for it to serve as a DDR ligand.

EXAMPLE 6

Fibrillar-Type Collagens may be Preferred DDR Ligands

Figure 10A:
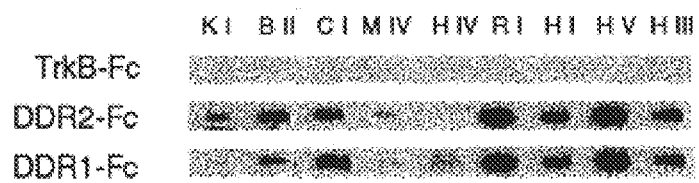
FIG. 10A—DDR binding to different types of commercially-derived collagens; note weaker binding of both DDR1 and DDR2 to network-forming collagen type IV as compared to rest of collagens, which are all examples of fibril-forming collagens (K, kangaroo tail; B, bovine nasal septum; C, calf skin; H: human placenta; R: rat tail; roman numerals represent biochemical types of collagen).
Figure 10B:
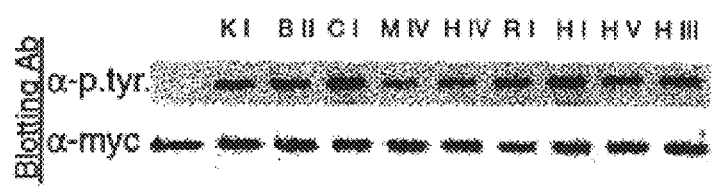
FIG. 10B—DDR1 phosphorylation induced by different types of collagen; note that network-forming type IV collagens consistently gave poorer phosphorylation responses.

We tested a variety of commercial collagens for their ability to bind and activate DDR receptors. Several of the major fibrillar collagens (Types I, II, III and V) exhibited marked binding to both DDR1 and DDR2 receptors (FIG. 10A), as well as relatively strong ability to induce DDR1 receptor phosphorylation (FIG. 10B); it should be noted that the same collagens from certain commercial suppliers ocasionally did not reveal detectable activity, suggesting that these collagens were inactivated for their DDR activity during purification or storage. The only non-fibrillar form of collagen tested (Type IV) revealed poor binding and somewhat weaker phosphorylating activity (FIGS. 10A and 10B). We tentatively conclude that fibril-forming collagens may be the preferred collagen ligands for the DDR receptors, although observed differences could clearly result from differential loss of activity during the purification process for the various collagens.

Figure 10C:
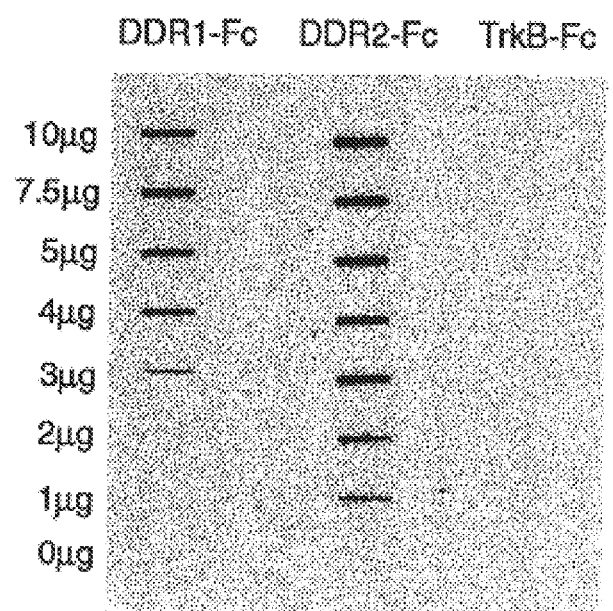
FIG. 10C—Differential slot-blot binding of DDR1 and DDR2 Rbodies to commercially-derived bovine dermal collagen I (Vitrogen). Binding was detectable for DDR2 at 1 ug loading and for DDR1 at 3 ug loading per slot.

We also noted slightly different preferences for DDR1 vs. DDR2 binding by the various collagens. For example, bovine dermal collagen type I appears to have about a three-fold preference for DDR2 as compared to DDR1 binding (FIG. 10C). Thus it appears possible that the DDR receptors can differentially distinguish between the various collagens.

It is also worth re-examining earlier results that different cell lines that bound the DDR Rbodies exhibited different ratios of binding to DDR1 as opposed to DDR2 (FIGS. 5A and 8A); for example, as noted above, A204 was preferentially bound by DDR2 while U373MG cells displayed rather equivalent binding to DDR1 and DDR2. These differences seem likely to reflect differential expression by the two cell lines of the various collagen types and/or different modifications of the collagens that may be differentially recognized by the two DDR receptors.

EXAMPLE 7

Dose-Dependence and Unusual Temporal Dependence of Collagen-Induced DDR Receptor Phosphorylation We next compared the dose and temporal dependence of DDR receptor activation by collagens to those previously observed for other receptor tyrosine kinases. Maximum induction of DDR1 receptor phosphorylation appeared to require between 1 and 10 micrograms/ml of collagen. Surprisingly, little receptor phosphorylation was noted in the first five minutes after collagen addition, with notable phosphorylation observed only after prolonged treatment and in some cases being maintained for at least 16 hours (FIG. 11B). The prolonged time for induction is in contrast to most other receptor tyrosine kinases, in which ligands induce maximum phosphorylation within minutes (e.g. Glass, D. et al., 1996, Cell 85: 513–523), and argues that the DDR receptors may not mediate acute responses but rather tonic ones reflecting the state of collagens in the extracellular matrix.

EXAMPLE 8

Immobilized Collagen Also Induces DDR1 Receptor Phosphorylation

Addition of monomeric collagen solubilized in acetic acid solutions to media containing cells, as done here for the phosphorylation assays depicted thus far, results in formation of fibrillar collagen as the added collagen is brought to neutral pH, and the prolonged time-course noted above may also depend on time-dependent changes in the configuration of the added collagen. Such considerations emphasize the artificial nature of the experimental methods used in the receptor phosphorylation assays, and thus an attempt was made to examine receptor phosphorylation in a more physiological manner. Thus, plates were coated with collagen to provide an immobilized ligand (albeit one enriched in monomer forms of collagen), and DDR1-expressing cells were then placed on top of this collagen. In this case, DDR1 phosphorylation was also induced with a protracted time-course, while no induction was observed when DDR1-expressing cells were placed on plates that had not been coated with collagen (FIG. 11C & 11D).

Our search for ligands utilized by the previously "orphan" DDR1 and DDR2 receptors appears to have resulted in an unexpected convergence between receptor tyrosine kinases long known to be activated by growth-factor-like peptides (Ullrich and Schlessinger, 1990), and extracellular matrix molecules which have previously been characterized as using the integrin class of cell surface receptors (Clark and Brugge, 1995). This convergence involves the realization that collagen, whose best characterized receptors to date include the α2β1 and α1β1 integrins (Kuhn and Eble, 1994), can also directly bind and activate the DDR receptor tyrosine kinases. There had been considerable prior evidence that collagens might utilize non-integrin receptors, mostly from studies of platelets, resulting in the suggestion of a two-step model in which integrin engagement precedes binding to a second unknown low-affinity signal transducing receptor that initiates intracellular tyrosine phosphorylations (Kehrel, 1995; Morton et al., 1995; Asselin et al., 1997).

The realization that the collagens act as DDR ligands began with a search for cell line sources of an activity that could specifically bind to DDR1 and DDR2, and also induce DDR1 receptor phosphorylation. Once sources were identified, a purification scheme was developed to purify to homogeneity the molecule accounting for this DDR binding and phosphorylating activity. This purification scheme depended on following the putative DDR ligand with a direct in vitro DDR1/DDR2 receptor binding assay. The putative DDR ligand, purified to homogenity from A204 cells by using the in vitro receptor binding assay, retained the ability to induce phosphorylation of cell-surface DDR1 receptors. This putative DDR ligand appeared to correspond to a hybrid type V/XI fibrillar collagen molecule previously shown (Kleman et al., 1992) to be produced by the A204 cells. Further evidence that collagens do indeed serve as direct DDR ligands came from the finding that the DDR binding activities seen in several cell lines could all be destroyed by collagenase treatment—although they were resistant to pepsin and trypsin degradation as is characteristic for collagens—and that production of this activity could be blocked by specific collagen synthesis inhibitors. In addition, a variety of commercially-derived collagens exhibited DDR binding and phosphorylating activity. Finally, the inability to dissociate DDR activity away from collagen using stringent conditions, together with the finding that purified collagen exhibited DDR activity only when assembled into triple-helices, strongly indicate that collagen itself corresponds to the DDR ligand we have identified in A204 and other cells.

It seems likely that collagens bind to DDR receptors in a fundamentally different manner than most conventional growth factors bind to receptor tyrosine kinases. These differences may account for the inability to detect binding of collagen passed over immobilized DDR receptors in a BIAcore assay, as well as the protracted time required to see DDR activation following collagen challenge. Both of these observations may reflect the slow association or low-affinity of the collagen-DDR interaction, or perhaps time-dependent reconfigurations of the collagen or DDR receptors that must occur before stable and functional complexes can form. Alternatively, these observations would also be consistent with the above-mentioned hypothesis that collagen must initially engage integrin receptors before it can activate a second, low-affinity signaling receptor (Kehrel, 1995; Morton et al., 1995; Asselin et al., 1997).

Understanding the physiological function of the DDRs as collagen receptors may depend upon precisely elucidating the nature of the collagen forms that can activate the DDR receptors, and how subtle differences in collagen structure might be distinguished by the DDR receptors, which seem to differentially bind to different collagens. Such precise understanding awaits further analysis, although our current findings indicate that the native, triple-helical configuration of collagen is required for it to serve as a DDR ligand, that fibril-forming collagens may be preferred over network-forming collagens, and that immobilized and possibly monomers of triple-helical collagen can bind and activate the DDR receptors. Understanding how the different collagen types and their various configurations and modifications (such as hydroxylations, glycosylations and cross-linkings) may result in quantitative differences in DDR activation requires further investigation, but may provide important clues into whether the DDR receptors are involved in sensing changes in collagen structure.

It is worth noting that the discoidin domains of the DDR receptors were thus named for their extensive homology to the discoidin I protein (Poole et al., 1981) of the slime mold, *Dictyostelium discoideum*. Discoidin I is a carbohydrate-binding lectin required for normal cell adhesion, migration and aggregation during slime mold development (Springer et al., 1984). Although our data clearly indicate that an intact and properly folded collagen peptide scaffold is required for DDR binding, it remains possible that the discoidin domains of the mammalian DDR receptors primarily bind to carbohydrate moieties presented on this scaffold. Such a possibility might reflect conservation of discoidin-domain containing proteins from slime mold to man in terms of their carbohydrate-binding properties as well as their roles in mediating adhesive interactions.

As noted, it is tempting to speculate that the primary role of the DDR receptors is to sense the quantity and configuration of collagens in the microenvironment, and then to regulate the cellular response in terms of adhesion, migration, differentiation, survival, proliferation, and perhaps even matrix production. For example, it is has long been appreciated that an increase in the polymerization state of microenvironmental collagens can inhibit cellular migration and proliferation (Schor, 1980; Martin and Sank, 1990; Koyama et al., 1996). Because of the existing synergies and interactions already identified between integrin and receptor tyrosine kinase signaling (Clark and Brugge, 1995), it is easy to imagine that collagen might signal via its two distinct receptor classes in an integrated manner to regulate the cellular response to the surrounding microenvironment. Interestingly, recent preliminary evidence suggests that DDR receptors may be dramatically regulated in situations in which collagens are thought to play important roles. For example, collagen type VI is induced in vitro during myoblast differentiation (Piccolo et al., 1995), and myoblast differentiation can be blocked in vitro and in vivo following treatment with collagen synthesis inhibitors (Saitoh et al., 1992). We have recently observed that DDR receptor mRNA levels are markedly induced during myoblast differentiation concomittantly with collagen synthesis. Another situation in which there is an intriguing preliminary link between DDR receptor expression and alterations in collagen synthesis and function involves pathological fibrosis. Excessive fibrosis involving alterations in the quantity and quality of collagen production marks many human diseases including hepatic cirrhosis, pulmonary fibrosis, chronic glomerulonephritis, systemic sclerosis, scarring, arterial restenosis and postsurgical adhesions (Varga and Jimenez, 1995). In the liver, the activated mesenchymal stellate cell has been identified as the primary source of the excessive matrix and collagen synthesis that causes hepatic scarring, and the activation state of the stellate cell seems to depend on changes in collagen structure in the surrounding microenvironment (Friedman, 1993). Thus, during liver injury, the stellate cell seems to be activated by replacement of network-forming collagens by fibril-forming collagens in the subendothelial space, and the activated stellate cell then seems to perpetuate the pathological state by continuing to over-produce fibril-forming collagens while secreting metalloproteases that specifically degrade network-forming collagens (Friedman, 1993). Preliminary evidence raises the intriguing possibility that collagen activation of DDR receptors plays a key role during stellate cell-driven fibrosis, and that appropriately manipulating these receptors may prove therapeutically beneficial in hepatic scarring and for other fibrotic diseases.

REFERENCES

Alves, F., Wolfgang, V., Mossie, K., Millauer, B., Hofler, H., and Ullrich, A. (1995). Distinct structural characteristics of discoidin I subfamily receptor tyrosine kinases and complementary expression in human cancer. Oncogene 10, 609–618.

Asselin, J., Gibbins, J. M., Acison, M., Han, Y. L., Morton, L. F., Farndale, R. W., Barnes, M. J., and Watson, S. P. (1997). A Collagen-Like Peptide Stimulates Tyrosine Phosphorylation of syk and Phospholipase Cγ2 in Platelets Independent of the Integrin α2β1. Blood 89, 1235–1242.

Bartley, T. D., Hunt, R. W., Welcher, A. A., Boyle, W. J., Parker, V. P., Lindberg, R. A., Lu, H. S., Colombero, A. M., Elliot, R. L., Guthrie, B. A., Hoist, P. L., Skrine, J. D., Toso, R. J., Zhang, M., Fernandez, E., Trail, G., Varnum, B., Yarden, Y., Hunter, T., and Fox, G. M. (1994). B61 is a ligand for the ECK receptor protein-tyrosine kinase. Nature 368, 558–560.

Beckmann, M. P., Cerretti, D. P., Baum, P., Vanden Bos, T., James, L., Farrah, T., Kozlosky, C., Hollingsworth, T., Shilling, H., Maraskovsky, E., Fletcher, F. A., Lhotak, V., Pawson, T., and Lyman, S. D. (1994). Molecular characterization of a family of ligands for the eph-related tyrosine kinase receptors. EMBO J. 13, 3757–3762.

Cheng, H. J., and Flanagan, J. G. (1994). Identification and cloning of EIF-1, a developmentally expressed ligand for the Mek4 and Sek receptor tyrosine kinases. Cell 79, 157–168.

Clark, E. A., and Brugge, J. S. (1995). Integrins and Signal Transduction Pathways: The Road Taken. Science 268, 233–239.

Davis, S., Aldrich, T. H., Jones, P. F., Acheson, A., Compton, D., Vivek, J., Ryan, T., Bruno, J., Radjiewski, C., Maisonpierre, P. C., and Yancopoulos, G. D. (1996). Isolation of Angiopoietin-1, a Ligand for the TIE2 Receptor by Secretion-Trap Expression Cloning. Cell 87, 1161–1169.

Davis, S., Gale, N. W., Aldrich, T. H., Maisonpierre, P. C., Lhotak, V., Pawson, T., Goldfarb, M., and Yancopoulos, G. D. (1994). Ligands for the EPH-related receptor tyrosine kinases that require membrane attachment or clustering for activity. Science 266, 816–819.

DiMarco, E., Cutuli, N., Guerra, L., Cancedda, R., and DeLuca, M. (1993). Molecular cloning of trkE, a novel trk-related putative tyrosine kinase receptor isolated from normal human keratinocytes and widely expressed by normal human tissues. J. Biol. Chem. 268, 24290–24295.

Fagerstam, L. (1991). A non-label technology for real time biospecific interaction analysis. Tech. Protein. Chem. 2, 65–71.

Friedman, S. L. (1993). The Cellular Basis Of Hepatic Fibrosis. N Engl J Med 328, 1828–1835.

Glass, D. J., Bowen, D. C., Stitt, T. N., Radziejewski, C., Bruno, J., Ryan, T. E., Gies, D. R., Shah, S., Mattsson, K., Burden, S. J., DiStefano, P. S., Valenzuela, D. M., DeChiara, T. M., and Yancopoulos, G. D. (1996). Agrin acts via a MuSK receptor complex. Cell 85, 513–523.

Jenny, R. J., Pittman, D. D., Toole, J. J., Kriz, R. W., Aldape, R. A., Hewick, R. M., Kaufman, R. J., and Mann, K. G. (1987). Complete cDNA and derived amino acid sequence of human factor V. Proc Natl Acad Sci USA 84, 4846–50.

Jing, S., Wen, D., Yu, Y., Holst, P., Luo, Y., Fang, M., Tamir, R., Antonio, L., Hu, Z., Cupples, R., Louis, J., Hu, S., Altrock, B., and Fox, G. (1996). GDNF-induced activation of the ret protein tyrosine kinase is mediated by GDNFR-alpha, a novel receptor for GDNF. Cell 85, 1113–1123.

Johnson, J., C., E. E., and Rutter, W. J. (1993). A receptor tyrosine kinase found in breast carcinoma cells has an extracellular discoidin I-like domain. Proc. Natl. Acad. Sci. USA 90, 5677–5681.

Johnsson, B., Lofas, S., and Lindquist, G. (1991). Immobilization of proteins to a carboxymethyldextran-modified gold surface for biospecific interaction analysis in surface plasmon resonance sensors. Anal. Biochem. 198, 268–277.

Karn, T., Uwe, H., Brauninger, A., Bohme, B., Wolf, G., Rubsamen-Waigmann, H., and Strebhardt, K. (1993). Structure, expression and chromosomal mapping of TKT from man and mouse: a new subclass of receptor tyrosine kinases with a factor VIII-like domain. Oncogene 8, 1333–3440.

Kehrel, B. (1995). Platelet receptors for collagens. Platelets 6: 11.

Kleman, J. -P., Hartmann, D. J., Ramirez, F., and van der Rest, M. (1992). The human rhabdomyosarcoma cell line A04 lays down a highly insoluble matrix composed mainly of alpha1 type-XI and alpha 2 type-V collagen chains. Eur. J. Biochem. 210, 329–335.

Koyama, H., Raines, E. W., Bornfeldt, K. E., Roberts, J. M., and Ross, R. (1996). Fibrillar Collagen Inhibits Arterial Smooth Muscle Proliferation through Regulation of Cdk2 Inhibitors. Cell 87, 1069–1078.

Kuhn, K., and Eble, J. (1994). The structural bases of integrin-ligand interactions. Trnds In Cell Biol. 4, 256–261.

Lai, C., and Lemke, G. (1991). An extended family of protein-tyrosine kinase genes differentially expressed in the vertebrate nervous system. Neuron 6, 691–704.

Lai, C., and Lemke, G. (1994). Structure and expression of the Tyro 10 receptor tyrosine kinase. Oncogene 9, 877–883.

Maisonpierre, P. C., Suri, C., Jones, P. F., Bartunkova, S., Wiegand, S. J., Radziejewski, C., Compton, D., McClain, J., Aldrich, T. H., Papadopoulos, N., Daly, T. J., Davis, S., Sato, T. N., and Yancopoulos, G. D. (1997). Angiopoietin-2, a Natural Antagonist for Tie2 That Disrupts in vivo Angiogenesis. Science 277, 55–60.

Martin, G. R. and Sank, A. C. (1990). Extracellular matrices, cells, and growth factors. In *Peptide Growth Factors and Their Receptors II.* p. 463–477.

Morton, L. F., Hargreaves, P. G., Farndale, R. W., D., Y. R., and Barnes, M. J. (1995). Integrin alpha 2 beta 1-independent activition of platelets by simple collagen-like peptides: Collagen tertiary (triple helical) and quaternary (Polymeric) structures are sufficient alone for alpha 2 beta 1-independent platelet reactivity. Biochem J 306, 337–344.

O'Reilly, D. R., Miller, L. K., and Luckow, V. A. (1992). Baculovirus Expression Vectors-A Laboratory Manual. (New York: W.H. Freeman).

Perez, J. L., X., S., Finkernagel, S., Sciorra, L., Jenkins, N. A., Gilbert, D. J., Copeland, N. G., and Wong, T. W. (1994). Identification and chromosomal mapping of a receptor tyrosine kinase with a putative phospholipid binding sequence in its ectodomain. Oncogene 9, 211–219.

Piccolo, S., Bonaldo, P., Vitale, P., Volpin, D., and Bressan, G. M. (1995). Transcriptional activation of the α1 (VI) Collagen Gene During Myoblast Differentiation is Mediated by Multiple GA Boxes. J. Biol. Chem. 270, 19583–19590.

Poole, S., Firtel, R. A., Lamar, E., and Rowekamp, W. (1981). Sequence and expression of the discoidin I gene family in *Dictyostelium discoideum*. J Mol Biol 153, 273–89.

Prockop, D. J., and Kivirrikko, K. I. (1995). Collagens: Molecular Biology, Diseases, and Potentials for Therapy. Annu. Rev. Biochem. 65, 403–34.

Saitoh, O., Periasemy, M., Kan, M., and Matsuda, R. (1992). Cis-4-hydroxy-L-Proline and Ethyl-3,4-Dihydroxybenzoate Prevent Myogenesis of C2C12 Muscle Cells and Block myoD1 and myogenin expression. Exp Cell Res 200, 70–76.

Sanchez, M. P., Tapley, P., Saini, S. S., He, B., Pulido, D., and Barbacid, M. (1994). Multiple tyrosine protein kinases in rat hippocampal neurons: Isolation of Ptk-3, a receptor expressed in proliferative zones of the developing brain. Proc. Natl. Acad. Aco. USA 91, 1819–1823.

Sato, K., T., T., Takayama, R., Ohtsuki, K., and Kawabata, M. (1995). Improved chromatographic purification of human and bovine type V collagen sub-molecular species and their subunits chains from conventional crude preparations. Application to cell-substratum adhesion assay for human umbilical vein endothelial cell. Journal of Chromatography B 663, 25–33.

Schor, S. L. (1980). Cell proliferation a migration on collagen substrata in vitro. J. Cell Science 41, 159–175.

Springer, W. R., Cooper, D. N., and Barondes, S. H. (1984). Discoidin I is implicated in cell-substratum attachment and ordered cell migration of *Dictyostelium discoideum* and resembles fibronectin. Cell 39, 557–64.

Stitt, T. N., Conn, G., Gore, M., Lai, C., Bruno, J., Radziejewski, C., Mattson, K., Fisher, J., Gies, D. R., Jones, P. F., Masiakowski, P., Ryan, T. E., Tobkes, N. J., Chen, D. H., DiStefano, P. S., Long, G. L., Basilico, C., Goldfarb, M. P., Lemke, G., Glass, D. J., and Yancopoulos, G. D. (1995). The anticoagulation factor protein S and its relative, Gas6, are ligands for the Tyro3/Axl family of receptor tyrosine kinases. Cell 80, 661–670.

Takagi, S., Tsuji, T., Amagai, T., Takamatsu, T., and Fujisawa, H. (1987). Specific cell surface labels in the visual centers of *Xenopus laevis* tadpole identified using monoclonal antibodies. Dev Biol 122, 90–100.

Treanor, J., Goodman, L., de Sauvage, F., Stone, D., Poulsen, K., Beck, C., Gray, C., Armanini, M., Pollock, R., Hefti, F., Phillips, H., Goddard, A., Moore, M., Buj-Bello, A., Davies, A., Asai, N., Takahashi, M., Vandlen, R., Henderson, C., and Rosenthal, A. (1996). Characterization of a multicomponent receptor for GDNF. Nature 382: 80–83.

Ullrich, A., and Schlessinger, J. (1990). Signal transduction by receptors with tyrosine kinase activity. Cell 61, 203–211.

Varga, J. and Jimenez, S. A. (1995). Modulation of Collagen Gene Expression: Its Relation to Fibrosis in Systemic Sclerosis and Other Disorders. Ann Intern Med. 122, 60–62.

Varnum, B. C., Young, C., Elliot, G., Garcia, A., Bartley, T. D., Fridell, Y. W., Hunt, R. W., Trail, G., Clogston, C., Toso, R. J., Yanagihara, D., Bennet, L., Sylber, M., Merewether, L. A., Tseng, A., Escobar, E., Liu, E. T., and Yamane, H. K. (1995). Axl receptor tyrosine kinase stimulated by the vitamin K-dependent protein encoded by growth-arrest-specific gene 6. Nature 373, 623–626.

Wood, W. I., Capon, D. J., Simonsen, C. C., Eaton, D. L., Citschier, J., Keyt, B., Seeburg, P. H., Smith, D. H., Hollingshead, P., and Wion, K. L. (1984). Expression of active human factor VIII from recombinant DNA clones. Nature 312, 330–7.

Zerlin, M., Julius, M. A., and Goldfarb, M. (1993). NEP: a novel receptor-like tyrosine kinase expressed in proliferating neuroepithelia. Oncogene 8, 2731–2739.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method of screening for a compound that competes with a collagen for binding to the extracellular domain of a Tyro-10 (DDR-2) receptor comprising:

a) contacting a known amount of the extracellular domain of Tyro-10 (DDR-2) receptor to the collagen under conditions in which the collagen is capable of binding to the extracellular domain;

b) determining the amount of the extracellular domain that binds to the collagen;

c) contacting a known amount of the extracellular domain of a Tyro-10 (DDR-2) receptor to collagen, in the presence of a test compound, under conditions in which the collagen is capable of binding to the extracellular domain;

d) determining the amount of the extracellular domain that binds to the collagen in the presence of the test compound;

e) comparing the amount of extracellular domain that binds to the collagen from (b) with the amount of extracellular domain that binds to the collagen from (d), wherein a lesser amount in (d) indicates that the test compound competes with collagen for binding to the extracellular domain of a Tyro-10 (DDR-2) receptor.

2. The method of claim 1, wherein the collagen is bound to a solid support.

3. The method of claim 2, wherein the extracellular domain is detectably labeled.

* * * * *